United States Patent
Wegmann et al.

(10) Patent No.: US 11,517,618 B2
(45) Date of Patent: Dec. 6, 2022

(54) METHOD OF INDUCING AN IMMUNE RESPONSE AGAINST HUMAN IMMUNODEFICIENCY VIRUS BY CO-LOCALIZED ADMINISTRATION OF VACCINE COMPONENTS

(71) Applicant: Janssen Vaccines & Prevention B.V., Leiden (NL)

(72) Inventors: Frank Wegmann, Leiden (NL); Gijs Hardenberg, Voorschoten (NL); Roland Christian Zahn, Rijnsburg (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 171 days.

(21) Appl. No.: 16/579,193

(22) Filed: Sep. 23, 2019

(65) Prior Publication Data
US 2020/0093917 A1    Mar. 26, 2020

(30) Foreign Application Priority Data

Sep. 25, 2018 (EP) .................................. 18196636

(51) Int. Cl.
| | |
|---|---|
| *A61K 39/00* | (2006.01) |
| *C07K 14/005* | (2006.01) |
| *A61K 39/21* | (2006.01) |
| *A61K 39/12* | (2006.01) |
| *C12N 7/00* | (2006.01) |
| *C12N 15/113* | (2010.01) |
| *C12N 15/861* | (2006.01) |

(52) U.S. Cl.
CPC .......... *A61K 39/21* (2013.01); *C12N 15/1132* (2013.01); *C12N 15/861* (2013.01); *C12N 2710/10043* (2013.01); *C12N 2710/24143* (2013.01)

(58) Field of Classification Search
CPC ...... C07K 14/005; A61K 39/21; A61K 39/12; C12N 2740/16134; C12N 7/00
See application file for complete search history.

(56) References Cited

U.S. PATENT DOCUMENTS

| | | | |
|---|---|---|---|
| 2012/0076812 A1 | 3/2012 | Barouch et al. | |
| 2016/0089432 A1* | 3/2016 | Barouch | A61K 39/12 424/188.1 |

FOREIGN PATENT DOCUMENTS

| | | |
|---|---|---|
| WO | 2003/104467 A1 | 12/2003 |
| WO | 2007/104792 A2 | 9/2007 |
| WO | 2008/107370 A1 | 9/2008 |
| WO | 2010/042942 A2 | 4/2010 |
| WO | 2011/106705 A2 | 9/2011 |
| WO | WO2011106705 * | 9/2011 |
| WO | 2012/082918 A1 | 6/2012 |
| WO | 2014/107744 A1 | 7/2014 |
| WO | 2015/189425 A1 | 12/2015 |
| WO | 2016/049287 A1 | 3/2016 |

OTHER PUBLICATIONS

Barouch et al., "Evaluation or a mosaic HIV-1 vaccine in a multicentre, randomised, douple-blind, placebo-controlled, pnase 1/2a clinical trial (APPROACH) and in rhesus monkeys (NHP 13-19)" Lancet, 2018; 392:232-243.*
Abbink et al, "Comparative Seroprevalence and Immunogenicity of Six Rare Serotype Recombinant Adenovirus Vaccine Vectors from Subgroups B and D," Journal of Virology, vol. 81, No. 9, pp. 4654-4663 (May 2007).
Barouch et al, "Evaluation of a mosaic HIV-1 vaccine in a multicentre, randomised, double-blind, placebo-controlled, phase 1/2a clinical trial (APPROACH) in rhesus monkeys (NHP 13-19)," The Lancet, vol. 392, pp. 232-243 (Jul. 2018).
Barouch et al, "Moasic HIV-1 Vaccines Expand the Breadth and Depth of Cellular Immune Responses in Rhesus Monkeys," Nature Medicine, vol. 16, pp. 319-323 (2010).
Barouch et al, "Protective Efficacy of a Global HIV-1 Mosaic Vaccine against Heterologous SHIV Challenges in Rhesus Monkeys," Cell, vol. 155, pp. 531-539 (Oct. 2013).
Bingley et al, "Influence of maternal age at delivery and birth order on risk of type 1 diabetes in childhood: prospective population based family study," BMJ, vol. 321, pp. 420-424 (Aug. 2000).
Gao et al, "Advances in HIV-1 Vaccine Development," Viruses, vol. 10, No. 167, pp. 1-26 (2018).
Havenga et al, "Novel replication-incompetent adenoviral B-group vectors: high vector stability and yield in PER.C6 cells," Journal of General Virology, vol. 87, pp. 2135-2143 (2006).
Jones et al, "Effects of Adsorption to Aluminum Salt Adjuvants on the Structure and Stability of Model Protein Antigens," The Journal of Biological Chemistry, vol. 280, No. 14, pp. 13406-13414 (2005).
Kovacs et al, "HIV-1 envelope trimer elicits more potent neutralizing antibody responses than monomeric gp120," Proceedings of the National Academy of Sciences of the United States of America, vol. 109, No. 30, pp. 12111-12116 (2012).
Nkolola et al, "Breadth of neutralizing Antibodies Elicited by Stable, Homogenous Clade A and Clade C HIV-1 gp140 Envelope Trimers in Guinea Pigs," Journal of Virology, vol. 84, No. 7, pp. 3270-3279 (2010).

(Continued)

Primary Examiner — Barry A Chestnut
(74) Attorney, Agent, or Firm — Ice Miller LLP

(57) ABSTRACT

Methods of inducing an immune response against human immunodeficiency virus (HIV) are described. In particular, methods of inducing an immune response against HIV by co-locally administering an immunogenically effective amount of an isolated HIV envelope (Env) polypeptide and an immunogenically effective amount of an adenovirus vector encoding an HIV antigen, e.g., Env antigen are described. The isolated HIV Env polypeptide and adenovirus vector can be administered in a single composition or in separate compositions, in which the composition or compositions do not contain an adjuvant.

15 Claims, 3 Drawing Sheets

Specification includes a Sequence Listing.

(56) References Cited

OTHER PUBLICATIONS

Written Opinion dated May 13, 2020 in International Application No. PCT/EP2019/075510.
Milicic et al., "Adjuvanting a viral vectored vaccine against pre-erythrocytic malaria," Scientific Reports, vol. 7, No. 7284, 12 pages (2017).

* cited by examiner

METHOD OF INDUCING AN IMMUNE RESPONSE AGAINST HUMAN IMMUNODEFICIENCY VIRUS BY CO-LOCALIZED ADMINISTRATION OF VACCINE COMPONENTS

CROSS-REFERENCE TO RELATED APPLICATION

This application claims priority under 35 U.S.C. § 119(b) to European Patent Application No. 18196636.7, filed Sep. 25, 2018, the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing_688097-859", creation date of Sep. 23, 2019, and having a size of 71.4 KB. The sequence listing submitted via EFS-Web is part of the specification and is herein incorporated by reference in its entirety.

BACKGROUND OF THE INVENTION

HIV-1 infection continues to be a significant cause of mortality and morbidity worldwide despite advances in antiretroviral therapy (ART) and implementation of various prevention strategies, due to, e.g., poor adherence and heterogeneous access. In 2015, over two million new HIV infections occurred, and 1.1 million people died of AIDS-related illness (www.who.int/hiv/data/en/). An effective HIV prophylactic vaccine is needed to control and ultimately end the global AIDS pandemic.

Vaccines aimed at controlling and/or preventing HIV infection are being developed. For example, a global vaccine aimed at protecting against all clades of HIV-1 through heterologous prime/boost regimens using viral vectors expressing mosaic Gag, Pol, and Env HIV antigens, designed to optimize coverage of global HIV-1 sequence diversity, in combination with trimeric envelope proteins to enhance humoral immunity is currently being developed. In particular, this vaccination regimen is currently the subject of ongoing clinical trials (e.g., ClinicalTrials.gov identifiers: NCT02315703 and NCT03060629). See, also Barouch et al. *The Lancet*, Volume 392, Issue 10143, P232-243, Jul. 21, 2018; WO2016049287. This vaccination regimen that is currently being tested in clinical studies consists of two intramuscular adenovirus vector prime immunizations followed by a boost with a combination of adenovirus vector and aluminum phosphate adjuvanted gp140 protein. In the boost immunization the adenovirus vector component and the aluminum phosphate adjuvanted gp140 protein are given in contralateral arms.

Adjuvants are commonly used in prophylactic vaccines to enhance antigen immunogenicity through induction of high-titer antibody responses with relatively low antigen amounts. This is however accompanied by increased vaccine complexity and reactogenicity, difficulties in vaccine licensing and in securing a supply of a stable quality. In the case of aluminum adjuvants (e.g. aluminum phosphate), the antigen is physically adsorbed to the adjuvant, a process that can affect the structure and stability of the adsorbed protein (e.g., Jones et al. *J. Biol. Chem.*, 280, 13406-13414 (2005)).

Concomitant administration of adenovirus vectors and adjuvanted protein is described in International Patent Application Publication WO 08/107370, and co-localized administration of two immunogenic vaccine components against respiratory antigens is described in International Patent Application Publication WO 15/189425. However, neither of these publications specifically mentions administration without an adjuvant in one of the original components.

Accordingly, there is a need in the art for improved methods and vaccine regimens to control and prevent HIV infection that address the aforementioned difficulties often associated with adjuvanted vaccines.

BRIEF DESCRIPTION OF THE INVENTION

The invention satisfies this need by providing a method of inducing an immune response against HIV in which immunogenic vaccine components can be administered in the absence of an adjuvant. In particular, the inventors surprisingly discovered that immunization with a combination of adenovirus vectors and aluminum phosphate adjuvanted HIV envelope polypeptide administered in contralateral arms could be replaced with co-localized (i.e., same site) administration of a combination of adenovirus vector(s) and unadjuvanted HIV envelope polypeptide to induce high-titer antibody responses as well as potent cellular immune responses against HIV, thereby eliminating the need for an adjuvant and potential adjuvant related reactogenicity, thus simplifying the regimen.

In one aspect, the invention relates to methods of inducing an immune response against human immunodeficiency virus (HIV) by co-local administration of adenovirus vector encoding an HIV Env antigen and an isolated HIV Env polypeptide in the absence of adjuvant.

In one embodiment, a method of inducing an immune response against human immunodeficiency virus (HIV) in a subject, comprises co-locally administering to the subject:
  (a) an immunogenically effective amount of an isolated HIV envelope (Env) polypeptide; and
  (b) an immunogenically effective amount of an adenovirus vector encoding an HIV Env antigen,
wherein the immunogenically effective amount of the isolated HIV Env polypeptide and the immunogenically effective amount of the adenovirus vector are co-locally administered in a single composition or in separate compositions, and wherein the composition or compositions do not comprise adjuvant.

In another embodiment, a method of inducing an immune response against a human immunodeficiency virus (HIV) in a subject, comprises co-locally administering to the subject:
  (a) an immunogenically effective amount of an isolated HIV envelope (Env) polypeptide; and
  (b) an immunogenically effective amount of an adenovirus vector encoding an HIV Env antigen,
wherein the immunogenically effective amount of the isolated HIV Env polypeptide and the immunogenically effective amount of the adenovirus vector are co-locally administered in a single composition or in separate compositions, and wherein the composition or compositions do not comprise adjuvant, wherein the adjuvant is or comprises aluminum phosphate, aluminum hydroxide, aluminum sulfate, aluminum oxide, calcium phosphate, liposomes, oil-in-water emulsion (e.g. MF59), water-in-oil emulsion, paraffin oil, toxoids, saponins or fractions thereof (e.g. Quil A, QS21, Matrix-M, Iscomatrix, ISCOM), IL-1, IL-2, IL-12, MoGM-CSF, lipid A or analogs or derivatives thereof (e.g. monophosphoryl lipid A (MPL), 3-de-O-acylated MPL (3D-MPL), GLA, SLA, PHAD, RC529, etc), CpG, or imidazoquinolines (e.g. imiquimod, R848), or any combination thereof. In certain embodiments, the composition or compositions do not comprise any adjuvant.

In some embodiments, the immunogenically effective amount of the isolated HIV Env polypeptide and the immunogenically effective amount of the adenovirus vector are administered co-locally for boosting immunization after administering to the subject an immunogenically effective amount of an adenovirus vector encoding an HIV Env antigen.

In some embodiments, the method further comprises administering an immunogenically effective amount of an adenovirus vector encoding a second HIV Env antigen together with the immunogenically effective amount of the adenovirus vector. This second HIV Env antigen could be encoded on the same vector as the HIV antigen, or encoded on a second adenovirus vector.

In some embodiments, the method further comprises administering an immunogenically effective amount of one or more adenovirus vectors encoding further HIV antigens. In certain embodiments thereof, such further HIV antigens comprise Gag and/or Pol antigens, or antigenic fragments thereof.

In some embodiments, the adenovirus vector(s) are adenovirus 26 (rAd26) vectors.

In some embodiments, the co-localized administration is by intramuscular injection to a single muscle.

In some embodiments, the immune response comprises a T-helper 1 (Th1) biased immune response.

The details of one or more embodiments of the invention are set forth in the description below. Other features and advantages will be apparent from the following detailed description, figures, and the appended claims.

BRIEF DESCRIPTION OF THE FIGURES

The foregoing summary, as well as the following detailed description of the invention, will be better understood when read in conjunction with the appended figures. It should be understood that the invention is not limited to the precise embodiments shown in the figures.

DETAILED DESCRIPTION OF THE INVENTION

Figure 1:
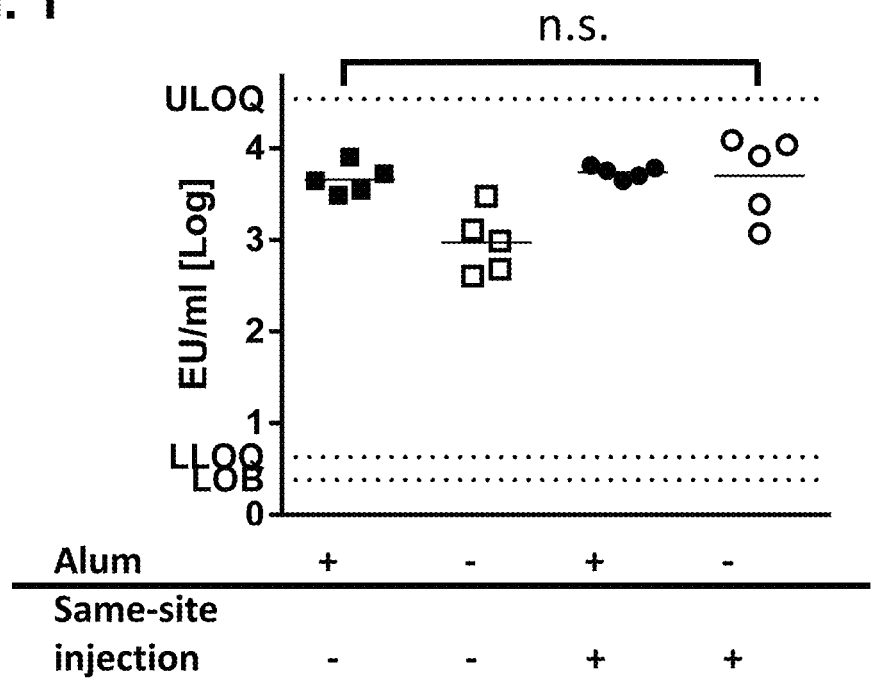
FIG. 1 shows clade C gp140 ELISA titers in serum at day 56 of the study described in Example 1; experimental groups are indicated below the graph; squares and circles represent individual animals and lines show geometric mean titers; animals in "alum+ same-site injection−" (i.e., alum-positive, same-site injection-negative) group are indistinguishable from the "alum− same-site injection+" (i.e., alum-negative, same-site injection-positive) group with regards to the induction of a clade C gp140-specific antibody response; ULOQ=upper limit of quantification, LLOQ=lower limit of quantification, LOB=Limit of Blanc, n.s.=not significant.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Unless otherwise stated, any numerical value, such as a concentration or a concentration range described herein, are to be understood as being modified in all instances by the term "about." Thus, a numerical value typically includes ±10% of the recited value. For example, a dosage of 100 µg includes 90 µg to 110 µg. As used herein, the use of a numerical range expressly includes all possible subranges, all individual numerical values within that range, including integers within such ranges and fractions of the values unless the context clearly indicates otherwise.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps. When used herein the term "comprising" can be substituted with the term "containing" or "including" or sometimes when used herein with the term "having."

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising," "containing," "including," and "having," whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, to whom will be or has been administered immunogenic components and/or compositions according to the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, and humans, etc., more preferably a human.

The invention relates to methods of inducing an immune response against human immunodeficiency virus (HIV) in a subject. According to embodiments of the invention, the method comprises co-locally administering to the subject:
(a) an immunogenically effective amount of an isolated HIV envelope (Env) polypeptide; and
(b) an immunogenically effective amount of an adenovirus vector encoding an HIV Env antigen,
wherein the immunogenically effective amount of the isolated HIV Env polypeptide and the immunogenically effective amount of the adenovirus vector are co-locally administered in a single composition or in separate compositions, and wherein the composition or compositions do not comprise adjuvant.

As used herein, the terms "co-locally administering," "co-localized administration," and "co-local administration" refer to administration of multiple vaccine components or compositions to a subject at the same or substantially the same location of the subject, such as to the same muscle or same site, e.g., skin, of the subject. The same location means the same or approximately same site. For example, in the case of parenteral administration (e.g., intramuscular injection), co-local administration means administration at the same or substantially the same site on the body of the subject, such as to the same site (e.g., by the same device, for instance a syringe or multi-chamber syringe) or, when using more than device (e.g., two syringes) within about 10 cm, and more preferably within about 5 cm or less, 2 cm or less, or 1 cm or less, or any distance in between in the same location (e.g., muscle). Co-local administration can be achieved by pre-mixing the vaccine components (e.g., isolated polypeptide and adenovirus vector) prior to administration, using two syringes, a multi-chamber syringe, or transdermal patch or other needleless device. For example, the vaccine components or compositions can be pre-mixed and administered in a single formulation, the vaccine components can be in a single composition, or the vaccine components or compositions can be administered in two separate formulations by a multi-chamber syringe. When using two or more syringes, co-localized administration should occur at substantially the same time, e.g., within one hour, such as within 1 minute, 5 minutes, 10 minutes, 15 minutes, 30 minutes, or one hour. Co-local administration is distinguished from contralateral administration and co-lateral administration, wherein multiple vaccine components or composition are co-administered to two separate sites of a subject, e.g., in two separate locations on the same side of the body, for instance two separate locations on the right arm (co-lateral administration) or two separate locations on opposite sides of the body, for instance two different arms (contralateral administration).

WO 2011/106705 discloses that a combination of a nucleic acid vaccine encoding an antigen of interest and protein vaccine that comprises the antigen, when co-administered at the same time, e.g. at the same site, results in an enhanced immune response in comparison to a prime/boost strategy wherein a DNA priming vaccine is followed by administration of a protein boosting vaccine; it thus discloses that co-injection of protein and DNA into the same muscle is immunogenic, however does not disclose that this is more immunogenic than co-administration at the same time into different muscles, so at best would suggest that DNA and protein co-local administration is an equivalent to co-administration at different sites. Moreover, all examples in WO 2011/106705 include at least one adjuvant (e.g. IL-12 encoded by the DNA vaccinations; and e.g. WO 2011/106705 example 3 demonstrates that the adjuvant IDRI EM005 is needed to induce potent Env-specific antibody titers (FIG. 10)). In contrast, the present inventors surprisingly describe herein that co-local administration of HIV Env protein and adenovirus vector encoding HIV Env is more immunogenic than co-administration (i.e. at the same time) into different sites, and moreover that co-local administration is surprisingly so effective that adjuvant is no longer needed for an effective immunization.

According to embodiments of the invention, composition(s) comprising the isolated HIV Env protein and adenovirus vector do not comprise an adjuvant. The terms "adjuvant" and "immune stimulant" are used interchangeably herein, and are defined as one or more substances that are added to or included in a composition with an immunogenic component (e.g., isolated polypeptide and/or adenovirus vector) for the specific purpose of stimulating or enhancing an immune response to the immunogenic component (e.g., isolated polypeptide and/or adenovirus vector). In this context, an adjuvant is a substance that is known to be safe and well-tolerated, and which has known efficacy for the specific purpose of enhancing or stimulating an immune response to an HIV antigen, e.g., an isolated HIV envelope polypeptide and/or adenovirus vector expressing an HIV antigen, particularly an HIV Env antigen, administered in the methods of the invention.

According to embodiments of the invention, adjuvants that can be omitted from (i.e. are not present in) the composition(s) to be administered to a subject according to the methods described herein include, but are not limited to, aluminum-based adjuvants, such as aluminum salts including aluminum phosphate (e.g., AdjuPhos®), aluminum hydroxide, aluminum sulfate, aluminum oxide; calcium phosphate; liposomes; oil-in-water emulsion (e.g. MF59); water-in-oil emulsion (e.g. TiterMax®); paraffin oil; toxoids; saponins or fractions thereof (e.g. Quil A, QS21, Matrix-M, Iscomatrix, and ISCOM); cytokines (e.g. IL-1, IL-2, IL-12, MoGM-CSF); lipid A or analogs or derivatives thereof (e.g. monophosphoryl lipid A (MPL), 3-de-O-acylated MPL (3D-MPL), GLA, SLA, PHAD, RC529, etc.), immunostimulatory nucleic acids (e.g., CpG oligodeoxynucleotides); imidazoquinolines (e.g. imiquimod, R848); Toll-like Receptor (TLR) agonists (e.g., TLR2, TLR3, TLR4, TLR5, TLR7, TLR8, TLR9, etc. agonists); AS01; AS02; AS03; AS04; AS15; AS25; polymer adjuvants (e.g., CRL-1005, Carbopol, adjuplex), GERBU, TERamide, PSC97B, Adjumer, PG-026, GSK-I, GcMAF, B-alethine, MPC-026, Betafectin, Adjuplex, army liposome formulation (ALF) (e.g., ALFA, ALFQ); and any combination thereof. In certain embodiments, the compositions do not include any adjuvant.

According to embodiments of the invention, the methods described herein can be used to induce an immune response against one or more clades of human immunodeficiency virus (HIV). HIV is a member of the genus Lentivirinae, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer, but are not limited to, HIV-1 and HIV-2, preferably HIV-1. HIV is categorized into multiple clades with a high degree of genetic divergence. As used herein, the term "HIV clade" or "HIV subtype" refers to related human immunodeficiency viruses classified according to their degree of genetic similarity. There are currently three groups of HIV-1 isolates: M, N and O. Group M (major strains) consists of at least ten clades, A through J. Group 0 (outer strains) can consist of a similar number of clades. Group N is a new HIV-1 isolate that has not been categorized in either group M or O. In certain embodiments, the methods of the invention generate an immune response against multiple clades of HIV-1, preferably including at least clades A, B and/or C.

HIV Antigens

As used herein, the terms "HIV antigenic polypeptide," "HIV antigenic protein," "HIV antigen," and "HIV immunogen" refer to a polypeptide capable of inducing an immune response, e.g., a humoral and/or cellular mediated response, against HIV in a subject. The antigenic polypeptide or antigen can be a protein of the HIV, a fragment or epitope thereof, or a combination of multiple HIV proteins or portions thereof that can induce an immune response or produce an immunity, e.g., protective immunity, against the HIV in a subject.

An HIV antigen can be any HIV-1 or HIV-2 antigen or fragment thereof. Examples of HIV antigens include, but are not limited to gag, pol, and env gene products, which encode structural proteins and essential enzymes. In particular, gag, pol, and env gene products are synthesized as polyproteins, which are further processed into multiple other protein products. The primary protein product of the gag gene is the viral structural protein gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41. Other examples of HIV antigens include gene regulatory proteins Tat and Rev; accessory proteins Nef, Vpr, Vif and Vpu; capsid proteins, nucleocapsid proteins, and p24 viral protein. Preferably, HIV antigens are HIV Gag, Pol, or Env antigens, or any portion or combination thereof, more preferably an HIV-1 Gag, Pol, or Env antigen, or any portion or combination thereof.

HIV antigens can also be mosaic HIV antigens. As used herein, "mosaic antigen" refers to a recombinant protein assembled from fragments of natural sequences. Mosaic antigens resemble natural antigens, but are optimized to maximize the coverage of potential T-cell epitopes found in the natural sequences, which improves the breadth and coverage of the immune response. Mosaic HIV antigens for use with the invention can be mosaic Gag, Pol, and/or Env antigens, preferably mosaic HIV-1 Gag, Pol, and/or Env antigens in which the sequences of gag, pol, and env gene products can be derived from one or more clades. For example, a mosaic HIV Env antigen specifically refers to a mosaic antigen comprising multiple epitopes derived from Env polyprotein sequences from one or more clades of HIV. Examples of mosaic HIV Gag, Pol and/or Env antigens that can be used in the invention include those described in, e.g., US20120076812; Barouch et al., Nat Med 2010, 16:319-323; and Barouch et al., Cell 155:1-9, 2013, all of which are incorporated herein by reference in their entirety. In particular, examples of mosaic HIV antigens suitable for use in the invention include, but are not limited to, mosaic HIV Env antigens with epitopes derived from the sequences of env gene products, such as those shown in SEQ ID NOs: 1-3; and mosaic Gag-Pol antigens with epitopes derived from the sequences of gag and pol gene products, such as those shown in SEQ ID NOs: 4 and 5, and combinations thereof.

According to embodiments of the invention, an adenovirus vector can encode any HIV Env antigen known in the art in view of the present disclosure.

In one embodiment, an HIV Env antigen encoded by an adenovirus vector, e.g., rAd26 vector, for use in the invention comprises the amino acid sequence of SEQ ID NO: 1.

In yet another embodiment, an HIV Env antigen encoded by an adenovirus vector, e.g., rAd26 vector, for use in the invention comprises the amino acid sequence of SEQ ID NO: 3.

In some embodiments, an adenovirus vector encoding an HIV Env antigen further encodes one or more additional HIV antigens. For example, an adenovirus vector can encode one or more additional Env antigens, or one or more other HIV antigens, such as HIV Gag and/or Pol antigens. Such additional HIV antigens can be encoded on the same adenovirus vector as the HIV Env antigen, or on one or more separate adenovirus vectors.

In other embodiments, an adenovirus vector encoding an HIV Env antigen is administered in combination with one or more additional adenovirus vectors (e.g., 1, 2, 3, 4, or more additional adenovirus vectors) encoding one or more additional HIV antigens, e.g., one or more additional HIV Env, Gag, and/or Pol antigens. Examples of other adenovirus vectors suitable for use in the methods of the invention include adenovirus vector encoding Gag-Pol antigens, such as those comprising the amino acid sequences of SEQ ID NO: 4 and/or SEQ ID NO: 5.

HIV Envelope Polypeptide

As used herein, each of the terms "envelope protein," "Env protein," "envelope polypeptide," and "Env" refers to a protein that is expressed on the envelope of an HIV virion and enables an HIV to target and attach to the plasma membrane of HIV infected cells, or a fragment or derivative thereof that can induce an immune response or produce an immunity against the HIV in a subject. The HIV env gene encodes the precursor protein gp160, which is proteolytically cleaved into the two mature envelope glycoproteins, gp120 and gp41. The cleavage reaction is mediated by a host cell protease, furin, at a sequence highly conserved in retroviral envelope glycoprotein precursors. More specifically, gp160 trimerizes to $(gp160)_3$ and then undergoes cleavage into the two noncovalently associated gp120 and gp41. Viral entry is subsequently mediated by a trimer of gp120/gp41 heterodimers. Gp120 is the receptor binding fragment, and binds to the CD4 receptor on a target cell that has such a receptor, such as, e.g., a T-helper cell. Gp41, which is non-covalently bound to gp120, is the fusion fragment and provides the second step by which HIV enters the cell. Gp41 is originally buried within the viral envelope, but when gp120 binds to a CD4 receptor, gp120 changes its conformation causing gp41 to become exposed, where it can assist in fusion with the host cell. Gp140 is the uncleaved ectodomain of trimeric gp160, i.e., $(gp160)_3$, that has been used as a surrogate for the native state of the cleaved, viral spike.

According to embodiments of the invention, an "HIV envelope polypeptide" can be a gp160, gp140, gp120, gp41 protein, combinations, fusions, truncations or derivatives thereof. For example, an "HIV envelope polypeptide" can include a gp120 protein noncovalently associated with a gp41 protein. It can also include a stabilized trimeric gp140 protein that can have or can be modified to include a trimerization domain that stabilizes trimers of gp140. Examples of trimerization domains include, but are not limited to, the T4-fibritin "foldon" trimerization domain; the coiled-coil trimerization domain derived from GCN4; and the catalytic subunit of *E. coli* aspartate transcarbamoylase as a trimer tag. An "HIV envelope polypeptide" can also be a truncated HIV envelope protein including, but not limited to, envelope proteins comprising a C-terminal truncation in the ectodomain (i.e. the domain that extends into the extracellular space), a truncation in the gp41, such as a truncation in the transmembrane domain of gp41, or a truncation in the cytoplasmic domain of gp41. An "HIV envelope polypeptide" can further be a derivative of a naturally occurring HIV envelope protein having sequence mutations, e.g., in the furin cleavage sites, and/or so-called SOSIP mutations.

HIV envelope polypeptide can be produced and isolated using any method known in the art in view of the present disclosure. For example, an HIV envelope polypeptide can be expressed from a host cell, preferably a recombinant host cell optimized for production of the envelope polypeptide. A leader/signal sequence can be operably linked to the N-terminus of the envelope polypeptide for maximal protein expression. The leader/signal sequence is usually cleaved from the nascent polypeptide during transport into the lumen of the endoplasmic reticulum. Any leader/signal sequence suitable for a host cell of interest can be used.

In some embodiments, the isolated HIV envelope polypeptide is a stabilized trimeric gp140 polypeptide, such as those described in Nkolola et al 2010, *J. Virology* 84(7): 3270-3279; Kovacs et al, *PNAS* 2012, 109(30):12111-6, WO 2010/042942 and WO 2014/107744, all of which are incorporated by reference in their entirety.

In some embodiments, an HIV Env polypeptide is a clade C gp140 protein, for instance Clade C gp140 polypeptide having the amino acid sequence of SEQ ID NO: 6.

In some embodiments, an HIV Env polypeptide is a mosaic Env polypeptide comprising multiple epitopes derived from one or more Env sequences of one or more HIV clades, for instance mosaic gp140 polypeptide having the amino acid sequence of SEQ ID NO: 7.

In other embodiments, one or more (e.g., two) HIV Env polypeptides, such as two gp140 polypeptides are administered together. For example, a clade C gp140 polypeptide having the amino acid sequence of SEQ ID NO: 6 and a mosaic gp140 polypeptide having the amino acid sequence of SEQ ID NO: 7 can be administered in combination.

Adenovirus Vectors

An adenovirus according to the invention belongs to the family of the *Adenoviridae*, and preferably is one that belongs to the genus *Mastadenovirus*. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu), or a simian adenovirus such as chimpanzee or gorilla adenovirus (ChAd, AdCh, or SAdV). In the invention, a human adenovirus is meant if referred to as Ad without indication of species, e.g. the brief notation "Ad26" means the same as HadV26, which is human adenovirus serotype 26. Also as used herein, the notation "rAd" means recombinant adenovirus, e.g., "rAd26" refers to recombinant human adenovirus 26.

An adenovirus vector can be based on any adenovirus serotype, preferably human adenovirus serotype, including but not limited adenovirus serotype 11, 26, 34, 35, 48, 49, 50, 52, etc., preferably rAd11, rAd26, rAd34, rAd35, rAd48, rAd49, rAd50, rAd52, etc. In certain preferred embodiments, the adenovirus vector is adenovirus 26 (Ad26). An advantage of human adenovirus serotype 26 is a low seroprevalence and/or low pre-existing neutralizing antibody titers in the human population, and such vectors have shown to generate good immune responses against different antigens in human clinical trials.

In a preferred embodiment, an adenovirus vector is an adenovirus 26 vector, particularly recombinant adenovirus 26 (rAd26) vector.

An "adenovirus capsid protein" refers to a protein on the capsid of an adenovirus (e.g., Ad26 vectors) that is involved in determining the serotype and/or tropism of a particular adenovirus. Adenoviral capsid proteins typically include the fiber, penton and/or hexon proteins. An rAd26 vector comprises at least hexon of Ad26, preferably at least hexon and fiber of Ad26. In preferred embodiments, the hexon, penton and fiber are of Ad26. Preferably, also the non-capsid proteins are from Ad26.

One of ordinary skill in the art will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of a first serotype with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad26 (i.e., the vector is rAd26). In some embodiments, the adenovirus is replication deficient, e.g., because it contains a deletion in the E1 region of the genome. For adenoviruses derived from Ad26 or other non-subgroup C adenoviruses, it is useful to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga, et al., 2006, *J Gen Virol* 87: 2135-43; WO 03/104467). However, such adenoviruses will not be capable of replicating in non-complementing cells that do not express the E1 genes of Ad5. Thus, in certain embodiments, the adenovirus is a human adenovirus of serotype 26, with a deletion in the E1 region into which the nucleic acid encoding one or more mosaic HIV antigens has been cloned, and with an E4 orf6 region of Ad5.

The preparation of recombinant adenoviral vectors is well known in the art. Preparation of rAd26 vectors is described, for example, in WO 2007/104792 and in Abbink et al., (2007) *Virol* 81(9): 4654-63. Exemplary genome sequences of Ad26 are found in GenBank Accession EF 153474 and in SEQ ID NO: 1 of WO 2007/104792. Examples of vectors useful for the invention for instance include those described in WO2012/082918, the disclosure of which is incorporated herein by reference in its entirety. Typically, an adenovirus vector useful in the invention is produced using a nucleic acid comprising the entire recombinant adenoviral genome (e.g., a plasmid, cosmid, or baculovirus vector).

In some embodiments, adenovirus vectors are replication deficient. In these embodiments, the virus is rendered replication deficient by deletion or inactivation of regions critical to replication of the virus, such as the E1 region. The regions can be substantially deleted or inactivated by, for example, inserting a gene of interest, such as a gene encoding an HIV antigen (usually linked to a promoter) within the region. In some embodiments, the vectors of the invention can contain deletions in other regions, such as the E3 region, or insertions of heterologous genes linked to a promoter within such regions. Mutations in the E3 region of the adenovirus need not be complemented by the cell line, since E3 is not required for replication.

A packaging cell line is typically used to produce sufficient amounts of adenovirus vectors. A packaging cell is a cell that comprises those genes that have been deleted or inactivated in a replication deficient vector, thus allowing the virus to replicate in the cell. Suitable packaging cell lines include, for example, PER.C6, 911, and HEK293.

According to embodiments of the invention, any of the HIV antigens described herein, such as HIV Env antigens, can be encoded by an adenovirus vector. Optionally, the heterologous gene encoding the HIV antigen can be codon-optimized to ensure proper expression in the treated host (e.g., human). Codon-optimization is a technology widely applied in the art. Examples of nucleic acid encoding HIV antigens that can be used in the adenovirus vectors of the invention include those show in SEQ ID NOs: 8-12. Typically, the heterologous gene encoding the HIV antigen is cloned into the E1 and/or the E3 region of the adenoviral genome. The heterologous gene encoding the HIV antigen can be under the control of (i.e., operably linked to) an adenovirus-derived promoter (e.g., the Major Late Promoter), or can be under the control of a heterologous promoter. Examples of suitable heterologous promoters include the cytomegalovirus (CMV) promoter and the Rous sarcoma virus (RSV) promoter. Preferably, the promoter is located upstream of the heterologous gene encoding the HIV antigen within an expression cassette.

Compositions and Immunogenic Compositions

According to embodiments of the invention, an immunogenically effective amount of an isolated HIV envelope polypeptide is co-locally administered to a subject with an immunogenically effective amount of an adenovirus vector encoding an HIV Env antigen. As used herein, "an immunogenically effective amount" or "immunologically effective amount" means an amount sufficient to induce a desired immune effect or immune response in a subject. In reference to an adenovirus vector encoding an HIV antigen or isolated HIV envelope polypeptide, an immunogenically effective amount or immunologically effective amount means an amount of the adenovirus vector or isolated HIV envelope polypeptide sufficient to induce a desired immune effect or immune response against HIV in a subject.

In one embodiment, an immunogenically effective amount means an amount sufficient to induce an immune response against HIV in a subject. In another embodiment, an immunogenically effective amount means an amount sufficient to produce immunity in a subject, e.g., provide a protective effect against HIV infection. An immunogenically effective amount can vary depending upon a variety of factors, such as the physical condition of the subject, age, weight, health, etc.; the particular application, whether inducing immune response or providing protective immunity; the specific adenovirus vector administered; the antigen encoded by the adenovirus vector administered; and the specific isolated HIV antigenic polypeptide administered. An immunogenically effective amount can readily be determined by one of ordinary skill in the art in view of the present disclosure.

An immunogenically effective amount can be administered in a single step (such as a single injection), or multiple steps (such as multiple injection), or in a single composition or multiple compositions. It is also possible to administer an immunogenically effective amount to a subject, and subsequently administer another dose of an immunogenically effective amount to the same subject, in a so-called prime-boost regimen. This general concept of a prime-boost regimen is well known to the skilled person in the vaccine field. Further booster administrations can optionally be added to the regimen, as needed.

An "immunogenic composition" or "vaccine composition" in particular is a composition comprising an immunogenically effective amount of a purified or partially purified adenovirus vector and/or an immunogenically effective amount of an isolated HIV envelope polypeptide. According to embodiments of the invention, the adenovirus vector and isolated HIV envelope polypeptide can be administered in the same composition (e.g., immunogenic composition or vaccine composition), or in separate compositions (e.g., immunogenic or vaccine compositions), wherein the composition(s) do not contain an adjuvant. Compositions and immunogenic or vaccine compositions can further comprise other HIV antigens, e.g., HIV gag, pol, and/or env antigens and/or adenovirus vectors expressing such antigens.

In one embodiment, an immunogenically effective amount of an adenovirus vector encoding an HIV Env antigen is administered in a composition (e.g., immunogenic composition) separate from an immunogenically effective amount of an isolated HIV envelope polypeptide. In such embodiments, the separate compositions are administered co-locally, i.e., to the same or substantially the same site of the subject, and compositions do not comprise an adjuvant.

In another embodiment, an immunogenically effective amount of an adenovirus vector encoding an HIV Env antigen is administered in the same composition (e.g., immunogenic composition) as an immunogenically effective amount of an isolated HIV envelope polypeptide, wherein the composition does not comprise an adjuvant. In such embodiments, the adenovirus vector and isolated HIV Env polypeptide can be pre-mixed to prepare a single formulation just prior to administration, or the adenovirus vector and isolated HIV Env polypeptide can be formulated in the same composition.

As general guidance, an immunogenically effective amount when used with reference to a recombinant viral vector can range from about $10^6$ viral particles to about $10^{12}$ viral particles, for example $10^6$, $10^7$, $10^8$, $10^9$, $10^{10}$, $10^{11}$, or $10^{12}$ viral particles. An immunogenically effective amount can be administered in a single composition, or in multiple compositions, such as 1, 2, 3, 4, 5, 6, 7, 8, 9, or 10 compositions (e.g., tablets, capsules or injectables), wherein the administration of the multiple capsules or injections collectively provides a subject with the immunogenically effective amount. In general, when used with reference to a polypeptide, such as an isolated antigenic polypeptide, an immunogenically effective amount can range from, e.g. about 0.3 to about 3000 microgram (µg), e.g. 1-1000 µg, e.g. 10-500 µg, e.g. about 1, 5, 10, 15, 50, 100, 150, 200, 250, 300, 350, 400, 450 or 500 µg, or any amount in between. When an immunogenically effective amount of a vaccine component is administered in multiple compositions, the multiple compositions are preferably administered co-locally per administration.

The preparation and use of compositions and immunogenic compositions are well known to those of ordinary skill in the art. Liquid pharmaceutical compositions generally include a liquid carrier such as water, petroleum, animal or vegetable oils, mineral oil or synthetic oil, preferably water or saline. Physiological saline solution, dextrose or other saccharide solution or glycols such as ethylene glycol, propylene glycol or polyethylene glycol can also be included. The compositions can comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, intradermal, oral, intravenous, cutaneous, mucosal (e.g., gut), intranasal or intraperitoneal routes.

The ability to induce or stimulate an anti-HIV immune response upon administration in an animal or human organism can be evaluated either in vitro or in vivo using a variety of assays which are standard in the art. For a general description of techniques available to evaluate the onset and activation of an immune response, see for example Coligan et al. (1992 and 1994, Current Protocols in Immunology; ed J Wiley & Sons Inc, National Institute of Health). Measurement of cellular immunity can be performed by measurement of cytokine profiles secreted by activated effector cells including those derived from CD4+ and CD8+ T-cells (e.g. quantification of IL-10 or IFN gamma-producing cells by ELISpot), by determination of the activation status of immune effector cells (e.g. T cell proliferation assays by a classical [$^3$H] thymidine uptake), by assaying for antigen-specific T lymphocytes in a sensitized subject (e.g. peptide-specific lysis in a cytotoxicity assay, etc.).

The ability to stimulate a humoral response can be determined by antibody binding and/or competition in binding (see for example Harlow, 1989, Antibodies, Cold Spring Harbor Press). For example, titers of antibodies produced in response to administration of a composition providing an immunogen can be measured by enzyme-linked immunosorbent assay (ELISA). The immune responses can also be measured by neutralizing antibody assay, where a neutralization of a virus is defined as the loss of infectivity through reaction/inhibition/neutralization of the virus with specific antibody. The immune response can further be measured by Antibody-Dependent Cellular Phagocytosis (ADCP) Assay.

Methods of Inducing an Immune Response

As used with reference to the methods described herein, "inducing an immune response" encompasses providing protective immunity and/or vaccinating a subject against an infection, such as a HIV infection, for prophylactic purposes, as well as causing a desired immune response or effect in a subject in need thereof against an infection, such as a HIV infection, for therapeutic purposes. As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all.

Administration of an immunogenically effective amount of an isolated HIV Env polypeptide and/or immunogenically effective amount of an adenovirus vector, or composition(s) thereof is typically intramuscular or subcutaneous. Thus, compositions or immunogenic compositions comprising such vaccine components are typically formulated for intramuscular or subcutaneous injection, and for the purposes of the invention formulated without adjuvants as indicated above, preferably without any adjuvant. However other modes of administration, such as intravenous, cutaneous, intradermal or nasal can be envisaged as well. For intravenous, cutaneous or subcutaneous injection, the adenovirus vector will be in the form of a parenterally acceptable aqueous solution which is pyrogen-free and has suitable pH, isotonicity and stability. Likewise, the isolated envelope polypeptide will be in the form of a parenterally acceptable solution having a suitable pH, isotonicity, and stability. Those of ordinary skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

In a particular embodiment, an immunogenically effective amount of an isolated HIV Env polypeptide and/or immunogenically effective amount of an adenovirus vector, or composition(s) thereof is administered via intramuscular administration. Intramuscular administration can be achieved by using a needle to inject a suspension of the adenovirus vectors and/or envelope polypeptides. An alternative is the use of a needleless injection device to administer the composition (using, e.g., Biojector™) or a freeze-dried powder containing the vaccine.

In some embodiments, an immunogenically effective amount of an isolated HIV Env polypeptide and immunogenically effective amount of an adenovirus vector are administered in the same composition co-locally by intramuscular administration, wherein the composition does not comprise an adjuvant. An example of co-local administration according to the invention is intramuscular injection of the composition or compositions in the deltoid of one arm of a subject.

In some embodiments, an immunogenically effective amount of an isolated HIV Env polypeptide and immunogenically effective amount of an adenovirus vector are administered in separate compositions co-locally by intramuscular administration, wherein none of the separate compositions comprises an adjuvant. In such embodiments, administration of the separate compositions can be via injection using a multi-chamber syringe, or via injection using two separate syringes to substantially the same-site, e.g., with the injections within 10 cm of each other into the same muscle.

In some embodiments, an immunogenically effective amount of an isolated HIV Env polypeptide and an immunogenically effective amount of an adenovirus vector encoding an HIV Env antigen are administered co-locally to a subject for priming immunization and for boosting immunization.

In some embodiments, an immunogenically effective amount of an isolated HIV Env polypeptide and an immunogenically effective amount of an adenovirus vector encoding an HIV Env antigen are administered co-locally to a subject for boosting immunization, after administering to the subject an immunogenically effective amount of an adenovirus vector encoding an HIV Env antigen. In other words, an immunogenically effective amount of an adenovirus vector encoding an HIV Env polypeptide can be administered for priming immunization, followed by co-local administration of an immunogenically effective amount of an isolated HIV Env polypeptide and an immunogenically effective amount of an adenovirus vector encoding an HIV Env antigen for boosting immunization. Preferably, such priming and boosting immunizations are administered by intramuscular administration. Adenovirus vectors and isolated HIV Env polypeptides that can be used in such prime-boost regimens are described in detail above. In particular embodiments, the same adenovirus vector, preferably an rAd26 vector, is used in the priming immunization and boosting immunization.

In certain embodiments, the priming immunization and/or the boosting administration, preferably both the priming and boosting administration, further comprise administering one or more adenovirus vectors that encode one or more further HIV antigens, e.g. Gag and/or Pol. The co-localized administration in the absence of adjuvant of the HIV Env antigen encoded by adenovirus and the isolated HIV Env polypeptide does not substantially lower the cellular immune response against such further HIV antigens.

The timing for administering priming and boosting immunizations is not particularly limited. For example, a vaccine composition can be administered for priming immunization, and re-administered prior to administration of a vaccine composition for boosting immunization. Further administrations of a vaccine composition for further boosting immunizations are also contemplated. In certain embodiments, a booster vaccine is first administered about 1-12 weeks, e.g., 1, 2, 3, 4, 5, 6, 7, 8, 9, 10, 11, or 12 weeks after a primer vaccine is initially administered. In other embodiments, a booster vaccine is first administered about 12-52 weeks, e.g., about 12, 14, 16, 18, 20, 22, 24, 26, 28, 30, 32, 34, 36, 38, 40, 42, 44, 46, 48, 50, or 52 weeks after a primer vaccine is initially administered. One of ordinary skill in the art will be able to vary the exact timing of the priming and boosting vaccines, frequency of administration thereof, dosage thereof, etc., based upon the teachings herein and general knowledge in the art.

In a particular embodiment, a method of inducing an immune response against HIV in a subject comprises co-locally administering to the subject an immunogenically effective amount of an isolated HIV Env polypeptide, and an immunogenically effective amount of an adenovirus vector, preferably an rAd26 vector, encoding an HIV Env antigen of SEQ ID NO: 1 in a single composition, or in separate compositions, wherein the composition or compositions do not comprise an adjuvant. The immunogenically effective amount of the isolated HIV Env polypeptide and the immunogenically effective amount of the adenovirus vector can be re-administered, preferably co-locally, to boost the immune response. Additionally or alternatively, the immunogenically effective amount of the isolated HIV Env polypeptide and the immunogenically effective amount of the adenovirus vector can be administered co-locally one or more times for boosting immunization after administering to the subject an immunogenically effective amount of an adenovirus vector encoding an HIV Env antigen, e.g., an HIV Env antigen of SEQ ID NO: 1. In certain embodiments, the isolated HIV Env polypeptide comprises SEQ ID NO: 6 or SEQ ID NO: 7, or comprises two isolated HIV Env polypeptides that comprise SEQ ID NOs: 6 and 7 respectively.

In another particular embodiment, a method of inducing an immune response against HIV in a subject comprises co-locally administering to the subject an immunogenically effective amount of an isolated HIV Env polypeptide, and an immunogenically effective amount of an adenovirus vector, preferably an rAd26 vector, encoding an HIV Env antigen of SEQ ID NO: 3 in a single composition, or in separate compositions, wherein the composition or compositions do not comprise an adjuvant. The immunogenically effective amount of the isolated HIV Env polypeptide and the immunogenically effective amount of the adenovirus vector can be re-administered, preferably co-locally, to boost the immune response. Additionally or alternatively, the immunogenically effective amount of the isolated HIV Env polypeptide and the immunogenically effective amount of the adenovirus vector can be administered co-locally one or more times for boosting immunization after administering to the subject an immunogenically effective amount of an adenovirus vector encoding an HIV Env antigen, e.g., an HIV Env antigen of SEQ ID NO: 3. In certain embodiments, the isolated HIV Env polypeptide comprises SEQ ID NO: 6 or SEQ ID NO: 7, or comprises two isolated HIV Env polypeptides that comprise SEQ ID NOs: 6 and 7 respectively.

In other embodiments, an adenovirus vector encoding an HIV Env antigen is administered together with one or more additional adenovirus vectors encoding one or more additional HIV antigens. The adenovirus vectors can be co-locally administered with an isolated HIV Env polypeptide in the same composition or in separate compositions, wherein the composition(s) do not comprise an adjuvant. The adenovirus vectors can be administered for priming immunization, and then re-administered co-locally with an isolated HIV Env polypeptide in the same composition or in separate compositions, wherein the composition(s) do not comprise an adjuvant. Preferably, the adenovirus vector and the one or more additional adenovirus vectors are rAd26 vectors.

In a particular embodiment, an adenovirus vector encoding an HIV Env antigen is administered together with an additional adenovirus vector encoding an additional HIV Env antigen. For example, an adenovirus vector, preferably rAd26 vector, encoding an HIV Env antigen of SEQ ID NO: 1 can be administered in combination with an additional adenovirus vector, preferably rAd26 vector, encoding an HIV Env antigen of SEQ ID NO: 3. Such adenovirus vectors can be administered co-locally with an isolated HIV Env polypeptide to induce an immune response against HIV in a subject. Such adenovirus vectors can also be administered for priming immunization, and re-administered co-locally with an isolated HIV Env polypeptide for boosting immunization. According to embodiments of the invention, when administered together co-locally, the adenovirus vectors and isolated HIV Env polypeptide are administered in the same composition or in separate compositions, wherein the composition or compositions do not comprise an adjuvant. In certain embodiments, the isolated HIV Env polypeptide comprises SEQ ID NO: 6 or SEQ ID NO: 7, or comprises two isolated HIV Env polypeptides that comprise SEQ ID NOs: 6 and 7 respectively.

In another particular embodiment, an adenovirus vector encoding an HIV Env antigen is administered together with one or more additional adenovirus vectors (e.g., 1, 2, 3, 4 or more additional adenovirus vectors) encoding one or more additional HIV antigens, e.g., HIV Env, Gag, and/or Pol antigens. Each adenovirus vector can encode a different HIV antigen, or combination of HIV antigens. For example, an adenovirus vector, preferably rAd26 vector, encoding an HIV Env antigen of SEQ ID NO: 1 can be administered in combination with a second adenovirus vector, preferably rAd26 vector, encoding an HIV Env antigen of SEQ ID NO: 3, a third adenovirus vector, preferably rAd26 vector, encoding an HIV Gag-Pol antigen of SEQ ID NO: 4, and a fourth adenovirus vector, preferably rAd26 vector, encoding an HIV Gag-Pol antigen of SEQ ID NO: 5. Such adenovirus vectors can be administered co-locally with an isolated HIV Env polypeptide to induce an immune response against HIV in a subject. Such adenovirus vectors can also be administered for priming immunization, and re-administered co-locally with an isolated HIV Env polypeptide for boosting immunization. When administered together co-locally, the adenovirus vectors and isolated HIV Env polypeptide are administered in the same composition or in separate compositions, wherein the composition or compositions do not comprise an adjuvant. In certain embodiments, the isolated HIV Env polypeptide comprises SEQ ID NO: 6 or SEQ ID NO: 7, or comprises two isolated HIV Env polypeptides that comprise SEQ ID NOs: 6 and 7 respectively.

According to embodiments of the invention, when adenovirus vector(s) are administered for priming immunization, and subsequently administered co-locally with an isolated HIV Env polypeptide in the absence of adjuvant for boosting immunization, the adenovirus vector(s) administered for priming immunization and boosting immunization can be the same or different. In certain embodiments they are the same.

In some embodiments, an immune response comprises a humoral immune response against HIV, preferably against multiple clades of HIV-1, such as at least clades A, B and/or C.

In some embodiments, an immune response comprises a cellular immune response against HIV, preferably against multiple clades of HIV-1, such as at least clades A, B and/or C.

In some embodiments, an immune response comprises a T-helper 1 (Th1) biased immune response. T lymphocytes expressing CD4 are also known as helper T cells, which produce cytokines. Helper T cells can be further subdivided into T-helper 1 (Th1) and T-helper 2 (Th2) cells, and the cytokines produced by such cells are known as Th1-type cytokines and Th2-type cytokines, respectively. Th1-type cytokines tend to produce the proinflammatory responses responsible for killing intracellular parasites and for perpetuating autoimmune responses. Interferon-γ is a primary Th1 cytokine. Excessive proinflammatory responses can lead to uncontrolled tissue damage, thus there needs to be a mechanism to counteract this effect. In particular, the Th2-type cytokines include interleukins (IL) 4, 5, and 13, which are associated with the promotion of IgE and eosinophilic responses in atopy, and also interleukin-10, which is considered a prototypical anti-inflammatory cytokine that can both impede pathogen clearance and ameliorate immunopathology. See, e.g., From: Bingley et al. *BMJ.* 2000 Aug. 12; 321(7258): 424.

Thus, in some embodiments, "a T-helper 1 biased immune response" or "Th1 biased immune response" refers to an immune response in which a greater amount (e.g., concentration) of cytokines produced by T-helper 1 (Th1) cells are produced, as compared to the amount (e.g., concentration) of cytokines produced by T-helper 2 (Th2) cells. Whether an immune response can be characterized as "Th1 biased" can be determined by measuring a concentration of one or more Th1 cytokines (e.g., IFN-γ) and one or more Th2 cytokines (e.g., IL-4, IL-5, IL-13, etc.), and comparing the concentration of Th1 cytokine(s) to the concentration of Th2 cytokine(s). In a particular embodiment, a Th1 biased immune response is identified by determining a ratio of the concentration of a Th1 cytokine (e.g., IFN-γ) to the concentration of a Th2 cytokine (e.g., IL-5) in a sample from a subject. For example, a ratio of the concentration of IFN-γ to the concentration of IL-5 of 1 to 100, such as 1, 10, 20, 30, 40, 50, 60, 70, 80, 90, or 100, or any value in between, more preferably greater than 1, even more preferably greater than 10, is indicative of a Th1 biased immune response.

The invention also relates to use of an immunogenically effective amount of an isolated HIV envelope (Env) polypeptide and an immunogenically effective amount of an adenovirus vector encoding an HIV Env antigen in the manufacture of a medicament for inducing an immune response against HIV in a subject by co-local administration of the isolated Env polypeptide and adenovirus vector to the subject, wherein the immunogenically effective amount of the isolated HIV Env polypeptide and the immunogenically effective amount of the adenovirus vector are in a single composition or separate compositions, and wherein the composition or compositions does not comprise adjuvant. All aspects and embodiments of the invention as described herein with respect to methods of inducing an immune response against a human immunodeficiency virus (HIV) can be applied to this aspect of the invention.

The invention further relates to an immunogenically effective amount of an isolated HIV envelope (Env) polypeptide and an immunogenically effective amount of an adenovirus vector encoding an HIV Env antigen for use in inducing an immune response against HIV in a subject by co-local administration of the isolated HIV Env polypeptide and the adenovirus vector to the subject, wherein the immunogenically effective amount of the isolated HIV Env polypeptide and the immunogenically effective amount of the adenovirus vector are in a single composition or separate compositions, and wherein the composition or compositions does not comprise adjuvant. All aspects and embodiments of the invention as described herein with respect to methods of inducing an immune response against a human immunodeficiency virus (HIV) can be applied to this aspect of the invention.

Embodiments

The invention also relates to the following non-limiting embodiments.

Embodiment 1 is a method of inducing an immune response against a human immunodeficiency virus (HIV) in a subject, the method comprising co-locally administering to the subject:

a. an immunogenically effective amount of an isolated HIV envelope (Env) polypeptide; and
b. an immunogenically effective amount of an adenovirus vector encoding an HIV Env antigen,
wherein the immunogenically effective amount of the isolated HIV Env polypeptide and the immunogenically effective amount of the adenovirus vector are co-locally administered in a single composition or in separate compositions, and wherein the composition or compositions do not comprise adjuvant.

Embodiment 2 is a method of inducing an immune response against a human immunodeficiency virus (HIV) in a subject, the method comprising co-locally administering to the subject:
a. an immunogenically effective amount of an isolated HIV envelope (Env) polypeptide; and
b. an immunogenically effective amount of an adenovirus vector encoding an HIV Env antigen,
wherein the immunogenically effective amount of the isolated HIV Env polypeptide and the immunogenically effective amount of the adenovirus vector are co-locally administered in a single composition or in separate compositions, and wherein the composition or compositions do not comprise adjuvant, wherein the adjuvant is or comprises aluminum phosphate, aluminum hydroxide, aluminum sulfate, aluminum oxide, calcium phosphate, liposomes, oil-in-water emulsion (e.g. MF59), water-in-oil emulsion, paraffin oil, toxoids, saponins or fractions thereof (e.g. Quil A, QS21, Matrix-M, Iscomatrix, and ISCOM), IL-1, IL-2, IL-12, MoGM-CSF, lipid A or analogs or derivatives thereof (e.g. monophosphoryl lipid A (MPL), 3-de-O-acylated MPL (3D-MPL), GLA, SLA, PHAD, RC529, etc), CpG, imidazoquinolines (e.g. imiquimod, R848), or any combination thereof.

Embodiment 2a is the method of embodiment 2, wherein the adjuvant is or comprises aluminum phosphate, aluminum hydroxide, aluminum sulfate, aluminum oxide, calcium phosphate, liposomes, oil-in-water emulsion (e.g. MF59), water-in-oil emulsion, paraffin oil, toxoids, saponins or fractions thereof (e.g. Quil A, QS21, Matrix-M, Iscomatrix, and ISCOM), IL-1, IL-2, IL-12, MoGM-CSF, lipid A or analogs or derivatives thereof (e.g. monophosphoryl lipid A (MPL), 3-de-O-acylated MPL (3D-MPL), GLA, SLA, PHAD, RC529, etc), CpG, imidazoquinolines (e.g. imiquimod, R848), Toll-like receptor agonists (e.g., TLR2, TLR3, TLR4, TLR5, TLR7, TLR8, TLR9, etc. agonists); AS01; AS02; AS03; AS04; AS15; AS25; polymer adjuvants (e.g., CRL-1005, Carbopol, Adjuplex), GERBU, TERamide, PSC97B, Adjumer, PG-026, GSK-I, GcMAF, B-alethine, MPC-026), Adjuvax, Betafectin, ALF, ALFA, or ALFQ, or any combination thereof.

Embodiment 3 is the method of embodiment 2 or 2a, wherein the composition or compositions do not comprise any adjuvant.

Embodiment 4 is the method of any one of embodiments 1-3, wherein the immunogenically effective amount of the isolated HIV Env polypeptide and the immunogenically effective amount of the adenovirus vector are administered co-locally for boosting immunization after administering to the subject an immunogenically effective amount of an adenovirus vector encoding an HIV Env antigen.

Embodiment 5 is the method of any one of embodiments 1-4, wherein the adenovirus vector is an adenovirus 26 (rAd26) vector.

Embodiment 6 is the method of any one of embodiments 1-5, further comprising administering an immunogenically effective amount of a second adenovirus vector encoding a second HIV Env antigen together with the immunogenically effective amount of the adenovirus vector.

Embodiment 7 is the method of embodiment 6, wherein the second adenovirus vector is an adenovirus 26 (rAd26) vector.

Embodiment 8 is the method of any one of embodiments 1-7, further comprising administering an immunogenically effective amount of one or more adenovirus vectors encoding further HIV antigens.

Embodiment 9 is the method of embodiment 8, wherein the further HIV antigens comprise Gag and/or Pol.

Embodiment 10 is the method of any one of embodiments 8 or 9, wherein the one or more adenovirus vectors encoding further HIV antigens are rAd26 vectors.

Embodiment 11 is the method of any one of embodiments 1-10, wherein the co-localized administration is by intramuscular injection to a single muscle.

Embodiment 12 is the method of any one of embodiments 1 to 11, wherein the immune response comprises a humoral immune response.

Embodiment 13 is the method of any one of embodiments 1 to 11, wherein the immune response comprises a cellular immune response.

Embodiment 14 is the method of any one of embodiments 1 to 13, wherein the immune response comprises a T-helper 1 (Th1) biased immune response.

Embodiment 15 is the method of any one of embodiments 8 to 10, wherein the immune response against the further HIV antigens is not substantially lowered as compared to administration of the HIV Env polypeptide adjuvanted with aluminum phosphate and the adenovirus vectors in contralateral sites of the subject.

The following examples of the invention are to further illustrate the nature of the invention. It should be understood that the following examples do not limit the invention and the scope of the invention is to be determined by the appended claims.

EXAMPLES

Example 1: Immunogenicity Study in Rabbits

Immunogenicity was evaluated in a prime-boost regimen with a 6 week interval in New Zealand White (NZW) rabbits. Rabbits were dosed on day 0 and day 42 with HIV-1 Clade C gp140 recombinant protein (10 μg) combined with 425 μg aluminium phosphate adjuvant (Adju-Phos®, 425 μg) or without adjuvant, and either co-administered with Ad26.Mos4.HIV vaccine in separate legs of the rabbits, or extemporaneously pre-mixed ('cage-side mixing') with the Ad26.Mos4.HIV vaccine and co-locally injected (i.e., same-site injection) into one leg of the rabbits. The Ad26.Mos4.HIV vaccine is composed of four recombinant Ad26 vectors each expressing a different HIV antigen or combination of HIV antigens, specifically Mos1.GagPol (SEQ ID NO: 4), Mos2.GagPol (SEQ ID NO: 5), Mos1.Env (SEQ ID NO: 1), and Mos2S.Env (SEQ ID NO: 3), and was administered at a total dose of $5 \times 10^9$ viral particles (vps) per administration. Animals were immunized by intramuscular administration of a 200 μL (co-administered in separate legs) or 400 μL volume (same-site injection) per quadriceps muscle.

Two weeks after the boost, serum antibodies were measured by enzyme-linked immunosorbent assay (ELISA) with vaccine autologous Clade C gp140 as coating antigen. The results are shown in FIG. 1. In particular, the results show that the clade C gp140 ELISA titers at day 56 of the study are indistinguishable between the group co-administered vector and adjuvanted protein in separate legs ("alum+ same-site-"), and the group co-locally administered (i.e., same-site injection) vector and protein without adjuvant ("alum- same-site+").

This study thus demonstrates that aluminum adjuvant is dispensable when the administered vaccine components (i.e., HIV Env antigen in the form of adenovirus vector and isolated polypeptide) are injected in the same-site, i.e., co-locally administered.

Example 2: Immunogenicity Study in Mice

Immunogenicity was evaluated in a prime-boost regimen with a 6 week interval in mice. CB6/F1 mice were immunized on day 0 and day 42 with HIV-1 Clade C gp140 recombinant protein co-locally injected (i.e., same-site injection) or separately administered in two different hind legs with Ad26.Mos4.HIV vaccine at 2 different doses, specifically 12.5 μg and 1.25 μg of Clade C gp140 recombinant protein. In the case of co-local injection, Ad26.Mos4.HIV and gp140 were extemporaneously pre-mixed ('cage side mixing'). The Clade C gp140 recombinant protein in the groups administered the recombinant protein and Ad26.Mos4.HIV vaccine (see Example 1 for a description) in the separate hind legs was adjuvanted with aluminum phosphate at corresponding dose levels of 21.25 μg and 2.125 μg, respectively. The Ad26.Mos4.HIV vaccine was administered at a total dose of $2.5 \times 10^9$ viral particles (vps) when administered with 12.5 μg of Clade C gp140 recombinant protein, and at a total dose of $2.5 \times 10^8$ vps when administered with 1.25 μg Clade C gp140 recombinant protein. Animals were immunized by intramuscular administration.

Figure 2:
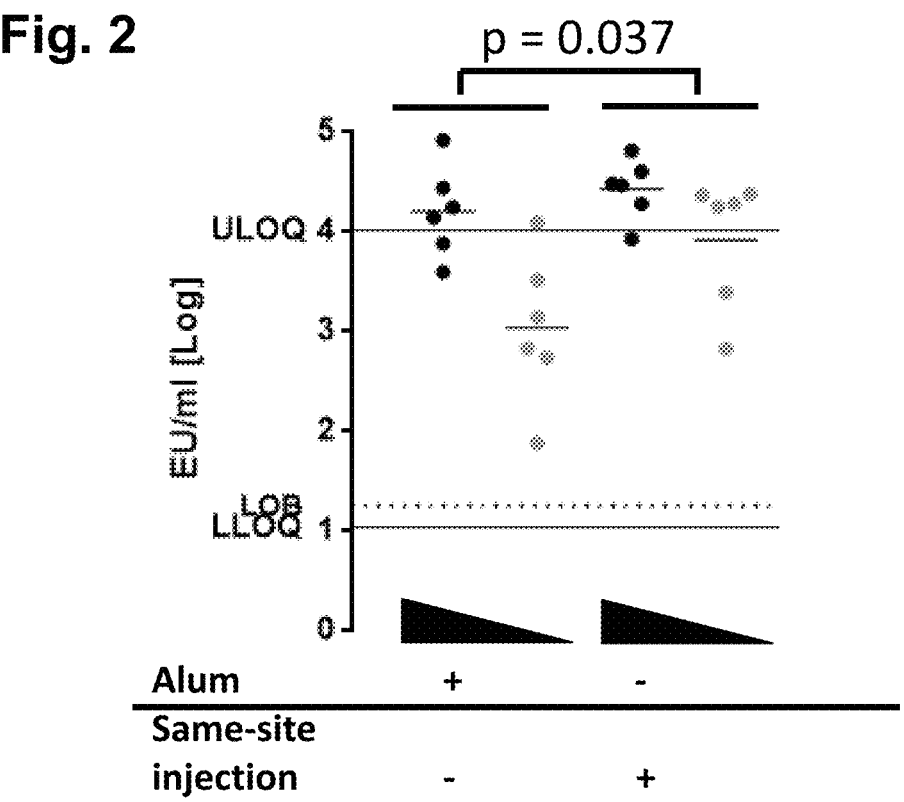
FIG. 2 shows clade C gp140 ELISA titers in serum at day 56 of the study described in Example 2 at two different dose levels of clade C gp140 recombinant protein; experimental groups are indicated below the graph; filled circles represent individual animals and lines show geometric mean titers; the black triangles indicate the different dose levels of clade C gp140 recombinant protein, with the high dose being 12.5 µg and the low dose being 1.25 µg; animals in "alum− same-site injection+" (i.e., alum-negative, same-site injection-positive) group show increased clade C gp140 ELISA titers compared to that of animals in "alum+ same-site injection−" (i.e., alum-positive, same-site injection-negative) group; ULOQ=upper limit of quantification, LLOQ=lower limit of quantification, LOB=Limit of Blanc.

Two weeks after the boost (i.e., at day 56), serum antibodies were measured by ELISA with vaccine-autologous Clade C gp140 as coating antigen. The results are shown in FIG. 2. In particular, the results show that the clade C gp140 ELISA titers in serum at day 56 in the group co-locally administered (i.e., same-site injection) vector and protein without adjuvant ("alum- same-site injection+") had increased clade C gp140 ELISA titers as compared to the group co-administered vector and adjuvanted protein in separate legs ("alum+ same-site injection-").

Figure 3:
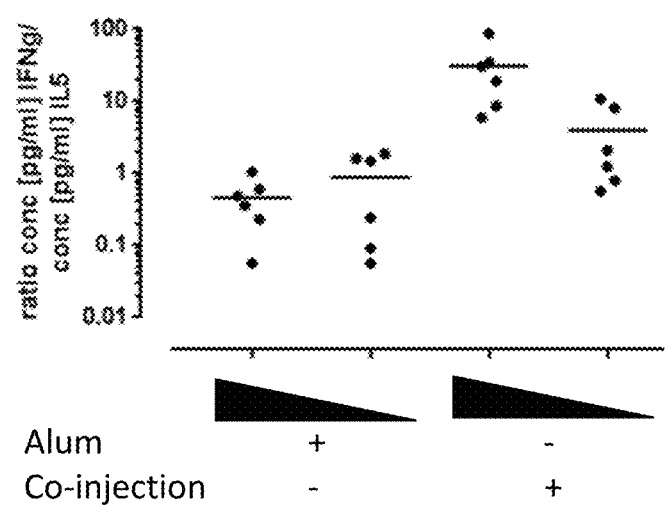
FIG. 3 shows the ratio of IFNγ to IL-5 in the splenocytes of mice re-stimulated in vitro with Clade C gp140 protein as described in Example 2; the black triangles indicate the different dose levels of clade C gp140 recombinant protein, with the high dose being 12.5 µg and the low dose being 1.25 µg; a high IFNγ/IL-5 ratio is indicative of a relative T-helper 1 (Th1) biased immune response; animals in the "alum− same-site injection+" (i.e., alum-negative, same-site injection-positive) group show a higher IFNγ/IL-5 ratio as compared to that of the animals in the "alum+ same-site injection−" group.

Additionally, splenocytes from the mice were re-stimulated in vitro with Clade C gp140 recombinant protein, and cytokines were analyzed in the supernatant 48 hours after the re-stimulation. The ratio of IFNγ to IL-5 was determined, and a high IFNγ/IL-5 ratio was indicated of a relative T-helper 1 (Th1) biased immune response. The results are shown in FIG. 3. The results demonstrate that co-local administration (i.e., same-site injection) of vector and protein without adjuvant induced a Th1-biased immune response as compared to co-administration of vector and adjuvanted protein in separate locations.

Figure 4:
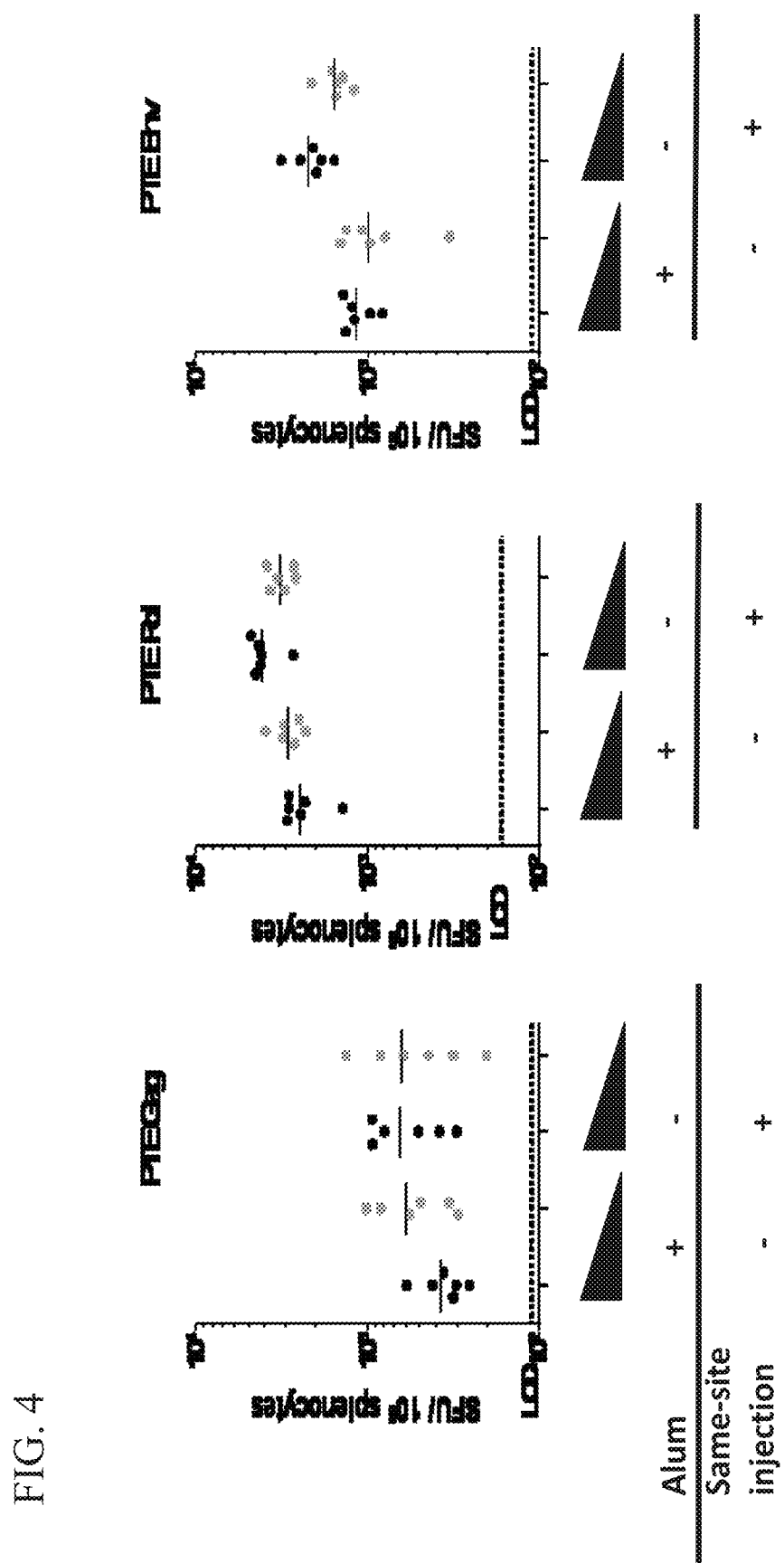
FIG. 4 shows results from an IFNγ Enzyme-Linked Immunospot (ELISpot) Assay on splenocytes obtained at day 56 of the study described in Example 2 using global potential T-cell epitope (PTE) peptide pools with Gag, Pol and Env, respectively; the black triangles indicate the different dose levels of clade C gp140 recombinant protein, with the high dose being 12.5 µg and the low dose being 1.25 µg; the results are shown as mean spot-forming units (SFU) per $10^6$ splenocytes; SFU values are similar or even higher in animals in the "alum− same-site injection+" (i.e., alum-negative, same-site injection positive) group compared to animals in the "alum+ same-site injection−" (i.e., alum-positive, same-site injection-negative) group, indicative of an intact cellular immune response; symbols represent the values for individual animals; horizontal lines indicate group geometric mean values and the dotted line represents the limit of detection (LOD).

Additionally, HIV-1-specific cellular immune responses were assessed by IFNγ ELISpot at day 56 of the study. Splenocytes from the mice were stimulated ex vivo using global potential T-cell epitope (PTE) peptide pools with Gag, Pol and Env respectively. The results are shown in FIG. 4. The results show a significantly higher cellular immune response for the Env antigen when adenovirus vector and protein were co-locally administered as compared to distal co-administration (p<0.0001, 2-way ANOVA with dose and mode of administration as explanatory factors). These results demonstrate that co-local administration (i.e., same-site injection) of adenovirus vector and protein without adjuvant does not decrease (but even increases) the immune response to co-administered antigens.

This study thus demonstrates that aluminum adjuvant is dispensable when the vaccine components are injected in the same-site, i.e., co-locally administered, and that co-local administration of HIV Env antigen in the form of adenovirus vector and isolated polypeptide results in an enhanced mean humoral response. This study also demonstrates that co-local administration of HIV Env antigen in the form of adenovirus vector and isolated polypeptide in the absence of adjuvant induces a more Th1-biased immune profile.

REFERENCES

1. US 2012/0076812
2. WO 2003/104467
3. WO 2007/104792
4. WO 2008/107370
5. WO 2010/042942
6. WO 2011/106705
7. WO 2014/107744
8. WO 2015/189425
9. WO 2016/049287
10. Abbink et al., (2007) *Virol* 81(9): 4654-63
11. Barouch et al. *The Lancet*, Volume 392, Issue 10143, P232-243, Jul. 21, 2018;
12. Barouch et al., Nat Med 2010, 16:319-323;
13. Barouch et al., Cell 155:1-9, 2013
14. Bingley et al. *BMJ*. 2000 Aug. 12; 321(7258): 424
15. Coligan et al. (1992 and 1994, Current Protocols in Immunology; ed J Wiley & Sons Inc, National Institute of Health).
16. Havenga, et al., 2006, *J Gen Virol* 87: 2135-43;
17. Jones et al. *J. Biol. Chem.*, 280, 13406-13414 (2005)
18. Kovacs et al, *PNAS* 2012, 109(30):12111-6,
19. Nkolola et al2010, *J. Virology* 84(7): 3270-3279

SEQUENCE LISTING

| SEQ ID NO: | Description | Sequence |
|---|---|---|
| 1 | Mos1Env | MRVTGIRKNYQHLWRWGTMLLGILMICSAAGKLWVTVYYGVPVWKEATTTLFCASDAKAYDTEVHNVWA THACVPTDPNPQEVVLENVTENFNMWKNNMVEQMHEDIISLWDQSLKPCVKLTPLCVTLNCTDDVRNVT NNATNTNSSWGEPMEKGEIKNCSFNITTSIRNKVQKQYALFYKLDVVPIDNDSNNTNYRLISCNTSVIT QACPKVSFEPIPIHYCAPAGFAILKCNDKKFNGTGPCTNVSTVQCTHGIRPVVSTQLLLNGSLAEEEVV IRSENFTNNAKTIMVQLNVSVEINCTRPNNNTRKSIHIGPGRAFYTAGDIIGDIRQAHCNISRANWNNT LRQIV EKLGKQFGNNKTIVFNHSSGGDPEIVMHSFNCGGEFFYCNSTKLFNSTWTWNNSTWNNTKRSNDTEEHI TLPCRIKQIINMWQEVGKAMYAPPIRGQIRCSSNITGLLLTRDGGNDTSGTEIFRPGGGDMRDNWRSEL YKYKVVKIEPLGVAPTKAKRRVVQSEKSAVGIGAVFLGELGAAGSTMGAASMTLTVQARLLLSGIVQQQ |

| SEQ ID NO: | Description | Sequence |
|---|---|---|
| | | NNLLRAIEAQQHLLQLTVWGIEQLQARVLAVERYLKDQQLLGIWGCSGKLICTTTVPWNASWSNKSLDK IWNNMTWMEWEREINNYTSLIYTLIEESQNQQEKNEQELLELDEWASLWNWFDISNWLW |
| 2 | Mos2Env | MRVRGIQRNWPQWWIWGILGEWMIIICRVMGNLWVTVYYGVPVWKEAKTTLFCASDAKAYEKEVHNVWA THACVPTDPNPQEMVLENVTENFNMWKNDMVDQMHEDIIRLWDQSLKPCVKLTPLCVTLECRNVRNVSS NGTYNIIHNETYKEMENCSFNATTVVEDRKQKVHALFYRLDIVPLDENNSSEKSSENSSEYYRLINCNT SAITQACPKVSFDPIPIHYCAPAGYAILKCNNKTFNGTGPCNNVSTVQCTHGIKPVVSTQLLLNGSLAE EEIIIRSENLTNNAKTIIVHLNETVNITCTRPNNNTRKSIRIGPGQTFYATGDIIGDIRQAHCNLSRDG WNKTLQGVKKKLAEHFPNKTINFTSSSGGDLEITTHSFNCRGEFFYCNTSGLFNGTYMPNGTNSNSSSN ITLPCRIXQIINMWQEVGRAMYAPPIAGNITCRSNITGLLLTRDGGSNNGVPNDTETFRPGGGDMRNNW RSELYKYKVVEVKPLGVAPTEAKRRVVESEKSAVGIGAVFLGILGAAGSTMGAASITLTVQARQLLSGI VQQQSNLLRAIEAQQHMLQLTVWGIKQLQTRVLAIERYLQDQQLLGLWGCSGKLICTTAVPWNTSWSNK SQTDIWDNMTWMQWDKEIGNYTGEIYRLLEESQNQQEKNEKDLLALDSWKNLWNWFDITNWLW |
| 3 | Mos2SEnv | MRVRGMLRNW QQWWIWSSLG FWMLMIYSVM GNLWVTVYYG VPVWKDAKTT LFCASDAKAY EKEVHNVWAT HACVPTDPNP QEIVLGNVTE NFNMWENDMV DQMHEDIISL WDASLEPCVK LTPLCVTLNC RNVRNVSSNG TYNIIHNETY KEMENCSFNA TTVVEDREQK VHALFYRLDI VPLDENNSSE ESSNSSEYY RLINCNTSAI TQACPKVSFD PIPIHYCAPA GYAILKCNNK TFNGTGPCNN VSTVQCTHGI KPVVSTQLLL NGSLAEEEII IRSENLTNNA KTIIVHLNET VNITCTRPNN NTRKSIRIGP GQTFYATGDI IGDIRQACHN LSRDGWNKTL QGVKKKLAEH FPNETIKFAP HSGGDLEITT HTFNCRGEFF YCNTSNLFNE SNIERNDSII TLPCRIKQII NMWQEVGRAI YAPPIAGNIT CRSNITGLLL TRDGGSNNGV PNDTETFRPG GGDMRNNWRS ELYKYKVVEV KPLGVAPTEA KRRVVEREKR AVGIGAVFLG ILGAAGSTMG AASITLTVQA RQLLSGIVQQ QSNLLRAIEA QQHMLQLTVW GIKQLQTRVL AIERYLQDQQ LLGLWGCSGK LICTTAVPWN TSWSNKSQTD IWDNMTWMQW DKEIGNYTGE IYRLLEESQN QQEKNEEDLL ALDSWNNLWN WFSISKWLWY IKIFIMIVGG LIGLRIIFAV LSIVNRVRQG Y |
| 4 | Mos1 GagPol | MGARASVLSGGELDRWEKIRLRPGGKKKYRLKHIVWASRELERFAVNPGLLETSEGCRQILGQLQPSLQ TGSEELRSLYNTVATLYCVHQRIEIKDTKEALEKIEEEQNKSKKKAQQAAADTGNSSQVSQNYPIVQNI QGQMVHQAISPRTLNAWVKVVEEKAFSPEVIPMFSALSEGATPQDLNTMLNTVGGHQAAMQMLKETINE EAAEWDRVHPVHAGPIAPGQMREPRGSDIAGTTSTLQEQIGWMTNNPPIPVGEIYKRWIILGLNKIVRM YSPVSILDIRQGPKEPFRDYVDRFYKTLRAEQASQDVKNWMTETLLVQNANPDCKTILKALGPAATLEE MMTACQGVGGPGHKARVLAEAMSQVTNSATIMMQRGNFRNQRKTVKCFNCGKEGHIAKNCRAPRKKGCW KCGKEGHQMKDCTERQANFLGKIWPSNKGRPGNFLQNRPEPTAPPEESFRFGEETTTPSQKQEPIDKEM YPLASLKSLFGNDPSSQMAPISPIETVPVKLKPGMDGPRVKQWPLTEEKIKALTAICEEMEKEGKITKI GPENPYNTPVFAIKKKDSTKWRKLVDFRELNKRTQDFWEVQLGIPHPAGLKKKKSVTVLAVGDAYFSVP LDEGFRKYTAFTIPSTNNETPGIRYQYNVLPQGWKGSPAIFQCSMTRILEPFRAKNPEIVIYQYMAALY VGSDLEIGQHRAKIEELREHLLKWGFTTPDKKHQKEPPFLWMGYELHPDKWTVQPIQLPEKDSWTVNDI QKLVGKLNWASQIYPGIKVRQLCKLLRGAKALTDIVPLTEEAELELAENREILKEPVHGVYYDPSKDLI AEIQKQGHDQWTYQIYQEPFKNLKTGKYAKMRTAHTNDVKQLTEAVQKIAMESIVIWGKTPKFRLPIQK ETWETWWTDYWQATWIPEWEFVNTPPLVKLWYQLEKDPIAGVETFYVAGAANRETKLGKAGYVTDRGRQ KIVSLTETTNQKTALQAIYLALQDSGSEVNIVTASQYALGIIQAQPDKSESELVNQIIEQLIKKERVYL SWVPAHKGIGGNEQVDKLVSSGIRKVLFLDGIDKAQEEHEKTHSNWRAMASDFNLPPVVAKEIVASCDQ CQLKGEAMHGQVDCSPGIWQLACTHLEGKIILVAVHVASGYIEAEVIPAETGQETAYFILKLAGRWPVK VIHTANGSNFTSAAVKAACWWAGIQQEFGIPYNPQSQGVVASMNKELKKIIGQVRDQAEHLKTAVQMAV FIHNFKRKGGIGGYSAGERIIDIIATDIQTKELQKQIIKIQNFRVYYRDSRDPIWKGPAKLLWKGEGAV VIQDNSDIKVVPRRKVKIIKDYGKQMAGADCVAGRQDED |
| 5 | Mos2 GagPol | MGARASILRGGKLDKWEKIRLRPGGKKHYMLKHLVWASRELERFALNPGLLETSEGCKQIIKQLQPALQ TGTEELRSLFNTVATLYCVHAEIEVRDTKEALDKIEEEQNKSQQKTQQAKEADGKVSQNYPIVQNLQGQ MVHQPISPRTLNAWVKVIEEKAFSPEVIPMFTALSEGATPQDLNTMLNTVGGHQAAMQMLKDTINEEAA EWDRLHPVHAGPVAPGQMREPRGSDIAGTTSNLQEQIAWMTSNPPIPVGDIYKRWIILGLNKIVRMYSP TSILDIKQGPKEPERDYVDRFFKTLRAEQATQCWKNWMTDTLLVQNANPDCKTILRALGPGATLEEMMT ACQGVGGPSHKARVLAEAMSQTNSTILMQRSNFKGSKRIVKCFNCGKEGHIARNCRAPRKKGCWKCGKE GHQMKDCTERQANFLGKIWPSHKGRPGNFLQSRPEPTAPPAESFRFEETTPAPKQEPKDREPLTSLRSL FGSDPLSQMAPISPIETVPVKLKPGMDGPKVKQWPLTEEKIKALVEICTEMEKEGKISKIGPENPYNTP IPAIKKKDSTKWRKLVDFRELNKRTQDFWEVQLGIPHPAGLKKKKSVTVLAVGDAYFSVPLDEDFRKYT AFTIPSINNETPGIRYQYNVLPQGWKGSPAIFQSSMTKILEPFRKQNPDIVIYQYMAALYVGSDLEIGQ HRTKIEELRQHLLRWGFTTPDKKHQKEPPFLWMGYELHPDKWTVQPIVLPEKDSWTVNDIQKLVGKLNW ASQIYAGIKVKQLCKLLRGTKALTEVVPLTEEAELELAENREILKEPVHGVYYDPSKDLIAEIQKQGQG QWTYQIYQEPFKNLKTGKYARMRGAHTNDVKQLTEAVQKIATESIVIWGKTPKFKLPIQKETWEAWWTE YWQATWIPEWEFVNTPPLVKLWYQLEKEPIVGAETFYVAGAANRETKLGKAGYVTDRGRQKVVSLTDTT NQKTALQATHLALQDSGLEVNIVTASQYALGIIQAQPDXSEESELVSQIIEQLIKKEKVYLAWVPAHKGI GGNEQVDKLVSRGIRKVLFLDGIDKAQEEHEKYHSNWRAMASEFNLPPIVAKEIVASCDKCQLKGEAIH GQVDCSPGIWQLACTHLEGKVILVAVHVASGYIEAEVIPAETGQETAYFLLKLAGRWPVKTIHTANGSN FTSATVKAACWWAGIKQEFGIPYNPQSQGVVASINKELKKIIGQVRDQAEHLKTAVQMAVFIHNFKRKG GIGEYSAGERIVDIIASDIQTKELQKQITKIQNFRVYYRDSRDPLWKGPAKLLWKGEGAVVIQDNSDIK VVPRRKAKIIRDYGKQMAGDDCVASRQDED |
| 6 | Clade C gp140 | AENLWVGNMW VTVYYGVPVW TDAKTTLFCA SDTKAYDREV HNVWATHACV PTDPNPQEIV LENVTENFNM WKNDMVDQMH EDIISLWDQS LKPCVKLTPL CVTLHCTNAT FKNNVTNDMN KEIRNCSFNT TTEIRDKKQQ GYALFYRPDI VLLKENRNNS NNSEYILINC NASTITQACP KVNFDPIPIH YCAPAGYAIL KCNNKTFSGK GPCNNVSTVQ CTHGIKPVVS TQLLLNGSLA |

| SEQ ID NO: | Description | Sequence |
|---|---|---|
|  |  | EKEIIIRSEN LTDNVKTIIV HLNKSVEIVC TRPNNNTRKS MRIGPGQTFY ATGDIIGDIR<br>QAYCNISGSK WNETLKRVKE KLQENYNNNK TIKFAPSSGG DLEITTHSFN CRGEFFYCNT<br>TRLFNNNATE DETITLPCRI KQIINMWQGV GRAMYAPPIA GNITCKSNIT GLLLVRDGGE<br>DNKTEEIFRP GGGNMKDNWR SELYKYKVIE LKPLGIAPTG AKERVVEREE RAVGIGAVFL<br>GFLGAAGSTM GAASLTLTVQ ARQLLSSIVQ QQSNLLRAIE AQQHMLQLTV WGIKQLQTRV<br>LAIERYLKDQ QLLGIWGCSG KLICTTNVPW NSSWSNKSQT DIWNNMTWME WDREISNYTD<br>TIYRLLEDSQ TQQEKNEKDL LALDSWKNLW SWFDISNWLW YIKSRIEGRG SGGYIPEAPR<br>DGQATVRKDG EWVLLSTFL |
| 7 | Mosaic gp140 | AGKLWVTVYY GVPVWKEATT TLFCASDAKA YDTEVHNVWA THACVPTDPN PQEVVLENVT<br>ENFNMWKNNM VEQMHEDIIS LWDQSLEPCV KLTPLCVTLN CTDDVRNVTN NATNTNSSWG<br>EPMEKGEIKN CSFNITTSIR NRVQKQYALF YKLDVVPIDN DSNNTNYRLI SCNTSVITQA<br>CPKVSFEPIP IHYCAPAGFA ILKCNDKKFN GTGPCTNVST VQCTHGIRPV VSTQLLLNGS<br>LAEEEVVIRS ENFTNNAKTI MVQLNVSVEI NCTRPNNNTR ESIHIGPGRA FYTAGDIIGD<br>IRQAHCNISR ANWNNTLRQI VEKLGKQFGN NKTIVFNHSS GGDPEIVMHS FNCGGEFFYC<br>NSTKLFNSTW TWNNSTWNNT KRSNDTEEHI TLPCRIXQII NMWQEVGKAM YAPPIRGQIR<br>CSSNITGLLL TRDGGNDTSG TEIFRPGGGD MRDNWRSELY KYKVVKIEPL GVAPTKAKER<br>VVQREERAVG IGAVFLGFLG AAGSTMGAAS MTLTVQARLL LSGIVQQQNN LLRAIEAQQH<br>LLQLTVWGIK QLQARVLAVE RYLKDQQLLG IWGCSGKLIC TTTVPWNASW SNKSLDKIWN<br>NMTWMEWERE INNYTSLIYT LIEESQNQQE KNEQELLELD KWASLWNWFD ISNWLWYIKS<br>RIEGRGSGGY IPEAPRDGQA YVREDGEWVL LSTFL |
| 8 | Mos1Env (nucleic acid) | ATGCGGGTGACCGGCATCCGGAAGAACTACCAGCACCTGTGGCGGTGGGGCACCATGCTGCTGGGCATC<br>CTGATGATTTGCTCTGCCGCCGGAAAGCTGTGGGTGACCGTGTACTACGGCGTGCCCGTGTGGAAAGAG<br>GCCACCACCACCCTGTTCTGCGCCAGCGACGCCAAGGCCTACGACACCGAGGTGCACAACGTGTGGGCC<br>ACCCACGCCTGCGTGCCCACCGACCCCAACCCCCAGGAAGTGGTCCTGGAAAACGTGACCGAGAACTTC<br>AACATGTGGAAGAACAACATGGTGGAGCAGATGCACGAGGACATCATCAGCCTGTGGGACCAGAGCCTG<br>AAGCCCTGCGTGAAGCTGACCCCCCTGTGCGTGACCCTGAACTGCACCGACGACGTGCGGAACGTGACC<br>AACAACGCCACCAACACCAACAGCAGCTGGGGCGAGCCTATGGAAAAGGGCGAGATCAAGAACTGCAGC<br>TTCAACATCACCACCTCCATCCGGAACAAGGTGCAGAAGCAGTACGCCCTGTTCTACAAGCTGGACGTG<br>GTGCCCATCGACAACGACAGCAACAACACCAACTACCGGCTGATCAGCTGCAACACCAGCGTGATCACC<br>CAGGCCTGCCCCAAGGTGTCCTTCGAGCCCATCCCCATCCACTACTGCGCCCCTGCCGGCTTCGCCATC<br>CTGAAGTGCAACGACAAGAAGTTCAACGGCACCGGCCCCTGCACCAACGTGAGCACCGTGCAGTGCACC<br>CACGGCATCCGGCCCGTGGTGTCCACCCAGCTGCTGCTGAACGGCAGCCTGGCCGAGGAAGAGGTGGTG<br>ATCAGAAGCGAGAATTTCACCAACAATGCCAAGACCATCATGGTGCAGCTGAACGTGAGCGTGGAGATC<br>AACTGCACCCGGCCCAACAACAACACCCGGAAGAGCATCCACATCGGCCCTGGCAGGGCCTTCTACACA<br>GCCGGCGACATCATCGGCGACATCCGGCAGGCCCACTGCAACATCAGCCGGGCCAACTGGAACAACACC<br>CTGCGGCAGATCGTGGAGAAGCTGGGCAAGCAGTTCGGCAACAACAAGACCATCGTGTTCAACCACAGC<br>AGCGGCGGAGACCCCGAGATCGTGATGCACAGCTTCAACTGTGGCGGCGAGTTCTTCTACTGCAACAGC<br>ACCAAGCTGTTCAACAGCACCTGGACCTGGAACAACTCCACCTGGAATAACACCAAGCGGAGCAACGAC<br>ACCGAAGAGCACATCACCCTGCCCTGCCGGATCAAGCAGATTATCAATATGTGGCAGGAGGTCGGCAAG<br>GCCATGTACGCCCCTCCCATCCGGGGCCAGATCCGGTGCAGCAGCAACATCACCGGCCTGCTGCTGACC<br>CGGGACGGCGGCAACGATACCAGCGGCACCGAGATCTTCCGGCCTGGCGGCGGAGATATGCGGGACAAC<br>TGGCGGAGCGAGCTGTACAAGTACAAGGTGGTGAAGATCGAGCCCCTGGGCGTGGCTCCCACCAAGGCC<br>AAGCGGCGGGTGGTGCAGAGCGAGAAGAGCGCCGTGGGCATCGGCGCCGTGTTTCTGGGCTTCCTGGGA<br>GCCGCCGGAAGCACCATGGGAGCCGCCAGCATGACCCTGACCGTGCAGGCCCGGCTGCTGCTGTCCGGC<br>ATCGTGCAGCAGCAGAACAACCTGCTCCGGGCCATCGAGGCCCAGCAGCACCTGCTGCAGCTGACCGTG<br>TGGGGCATCAAGCAGCTGCAGGCCAGGGTGCTGGCCGTGGAGAGATACCTGAAGGATCAGCAGCTCCTG<br>GGGATCTGGGGCTGCAGCGGCAAGCTGATCTGCACCACCAACGTGCCCTGGAACGCCAGCTGGTCCAAC<br>AAGAGCCTGGACAAGATCTGGAACAATATGACCTGGATGGAATGGGAGCGCGAGATCAACAATTACACC<br>AGCCTGATCTACACCCTGATCGAGGAAAGCCAGAACCAGCAGGAAAAGAACGAGCAGGAACTGCTGGAA<br>CTGGACAAGTGGGCCAGCCTGTGGAACTGGTTCGACATCAGCAACTGGCTGTGG |
| 9 | Mos2Env (nucleic acid) | ATGAGAGTGCGGGGCATCCAGCGGAACTGGCCCCAGTGGTGGATCTGGGGCATCCTGGGCTTTTGGATG<br>ATCATCATCTGCCGGGTGATGGGCAACCTGTGGGTGACCGTGTACTACGGCGTGCCCGTGTGGAAAGAG<br>GCCAAGACCACCCTGTTCTGCGCCAGCGACGCCAAGGCCTACGAGAAAGAGGTGCACAACGTGTGGGCC<br>ACCCACGCCTGCGTGCCCACCGACCCCAACCCCCAGGAAATGGTCCTGGAAAACGTGACCGAGAACTTC<br>AACATGTGGAAGAACGACATGGTGGACCAGATGCACGAGGACATCATCCGGCTGTGGGACCAGAGCCTG<br>AAGCCCTGCGTGAAGCTGACCCCCCTGTGCGTGACCCTGGAATGCCGGAACGTGAGAAACGTGAGCAGC<br>AACGGCACCTACAACATCATCCACAACGAGACCTACAAAGAGATGAAGAACTGCAGCTTCAACGCCACC<br>ACCGTGGTGGAGGACCGGAAGCAGAAGGTGCACGCCCTGTTCTACCGGCTGGACATCGTGCCCCTGGAC<br>GAGAACAACAGCAGCGAGAGTCAGCGAGAACAGCTCCGGTACAGACTGATCAACTGCAACACCAGCACC<br>AGCGCCATCACCCAGGCCTGCCCCAAGGTGTCCTTCGACCCCATCCCCATCCACTACTGCGCCCCTGCC<br>GGCTACGCCATCCTGAAGTGCAACAACAAGGACTTCAACGGCACCGGCCCCTGCAACAACGTGAGCACC<br>GTGCAGTGCACCCACGGCATCAAGCCCGTGGTGTCCACCCAGCTGCTGCTGAACGGCAGCCTGGCCGAG<br>GAAGAGATCATCATCCGGTCCGAGAACCTGACCAACAACGCCAAGACCATCATCGTGCACCTGAATGAG<br>ACCGTGAACATCACCTGCACCCGGCCCAACAACAACACCCGGAAGAGCATCCGGATCGGCCCTGGCCAG<br>ACCTTTTACGCCACCGGCGACATCATCGGCGACATCCGGCAGGCCCACTGCAACATCTCCGAGGGACGGC<br>TGGAACAAGACCCTGCAGGGCGTGAAGAAGAAGCTGGCCGAGCACTTCCCCAATAAGACCATCAACTTC<br>ACCAGCAGCAGCGGCGGAGACCTGGAAATCACCACCCACAGCTTCAACTGCAGGGGCGAGTTCTTCTAC<br>TGCAATACCTCCGGCCTGTTCAATGGCACCTACATGCCCAACGGCACCAACAGCAACAGCAGCAGCAAC<br>ATCACCCTGCCCTGCCGGATCAAGCAGATCATCAATATGTGGCAGGAGGTCGGCAGGGCCATGTACGCC<br>CCTCCCATCGCCGGCAATATCACCTGCCGGTCCAACATCACCGGCCTGCTGCTGACCAGGGACGGCGGC |

SEQUENCE LISTING

| SEQ ID NO: | Description | Sequence |
|---|---|---|
| | | AGCAACAACGGCGTGCCTAACGACACCGAGACCTTCCGGCCTGGCGGCGGAGATATGCGGAACAACTGG<br>CGGAGCGAGCTGTACAAGTACAAGGTGGTGGAGGTGAAGCCCCTGGGCGTGGCTCCTACCGAGGCCAAG<br>CGGCGGGTGGTGGAGAGCGAGAAGAGCGCCGTGGGCATCGGCGCCGTGTTTCTGGGCATTCTGGGAGCC<br>GCCGGAAGCACCATGGGAGCCGCCAGCATCACCCTGACCGTGCAGGCCCGGCAGCTGCTGTCCGGCATC<br>GTGCAGCAGCAGAGCAACCTGCTGAGAGCCATCGAGGCCCAGCAGCACATGCTGCAGCTGACCGTGTGG<br>GGCATCAAGCAGCTGCAGACCCGGGTGCTGGCCATCGAGAGATACCTGCAGGATCAGCAGCTCCTGGGC<br>CTGTGGGGCTGCAGCGGCAAGCTGATCTGCACCACCGCCGTGCCCTGGAACACCAGCTGGTCCAACAAG<br>AGCCAGACCGACATCTGGGACAACATGACCTGGATGCAGTGGGACAAAGAGATCGGCAACTACACCGGC<br>GAGATCTACAGGCTGCTGGAAGAGAGCCAGAACCAGCAGGAAAAGAACGAGAAGGACCTGCTGGCCCTG<br>GACAGCTGGAAGAACCTGTGGAACTGGTTCGACATCACCAACTGGCTGTGG |
| 10 | Mos2SEnv (nucleic acid) | ATGAGAGTGCGGGGCATGCTGAGAAACTGGCAGCAGTGGTGGATCTGGTCCAGCCTGGGCTTCTGGATG<br>CTGATGATCTACAGCGTGATGGGCAACCTGTGGGTCACCGTGTACTACGGCGTGCCCGTGTGGAAGGAC<br>GCCAAGACCACCCTGTTTTGCGCCTCCGATGCCAAGGCCTACGAGAAAGAGGTGCACAACGTCTGGGCC<br>ACCCACGCCTGTGTGCCCACCGACCCCAATCCCCAGGAAATCGTCCTGGGCAACGTGACCGAGAACTTC<br>AACATGTGGAAGAACGACATGGTCGATCAGATGCACGAGGACATCATCTCCCTGTGGGACGCCTCCCTG<br>GAACCCTGCGTGAAGCTGACCCCTCTGTGCGTGACCCTGAACTGCCGGAACGTGCGCAACGTGTCCAGC<br>AACGGCACCTACAACATCATCCACAACGAGACATACAAAGAGATGAAGAACTGCAGCTTCAACGCTACC<br>ACCGTGGTCGAGGACCGGAAGCAGAAGGTGCACGCCCTGTTCTACCGGCTGGACATCGTGCCCCTGGAC<br>GAGAACAACAGCAGCGAGAAGTCCTCCGAGAACAGCTCCGAGTACTACAGACTGATCAACTGCAACACC<br>AGCGCCATCACCCAGGCCTGCCCCAAGGTGTCCTTCGACCCTATCCCCATCCACTACTGCGCCCCTGCC<br>GGCTACGCCATCCTGAAGTGCAACAACAAGGACCTTCAATGGCACCGGCCCCTGCAACAATGTGTCCACC<br>GTGCAGTGCACCCACGGCATCAAGCCCGTGGTGTCTACCCAGCTGCTGCTGAACGGCAGCCTGGCCGAG<br>GAAGAGATCATTATCAGAAGCGAGAACCTGACCGACAACAAGACCATCATCGTCCACCTGAACGAA<br>ACCGTGAACATCACCTGTACCCGGCCTAACAACAACACCCGGAAGTCCATCCGGATCGGCCCTGGCCAG<br>ACCTTTTACGCCACCGGCGATATTATCGGCGACATCCGGCAGGCCCACTGCAATCTGAGCCGGGACGGC<br>TGGAACAAGACACTGCAGGGCGTCAAGAAGAAGCTGGCCGAACACTTCCCTAACAAGACTATCAAGTTC<br>GCCCCTCACTCTGGCGGCGACCTGGAAATCACCACCCACACCTTCAACTGTCGGGGCGAGTTCTTCTAC<br>TGCAATACCTCCAACCTGTTCAACGAGAGCAACATCGAGCGGAACGACAGCATCATCACACTGCCTTGC<br>CGGATCAAGCAGATTATCAATATGTGGCAGGAAGTGGGCAGAGCCATCTACGCCCCTCCAATCGCCGGC<br>AACATCACATGCCGGTCCAATATCACCGGCCTGCTGCTCACCAGAGATGGCGGCTCCAACAATGGCGTG<br>CCAAACGACACCGAGACATTCAGACCCGGCGGAGGCGACATGCGGGACAATTGGCGGAGCGAGCTGTAC<br>AAGTACAAGGTGGTGGAAGTGAAGCCCCTGGGCGTGGCCCCTACCGAGGCCAAGAGAAGAGTGGTCGAA<br>CGCGAGAAGCGGGCCGTGGGAATCGGAGCCGTGTTTCTGGGAATCCTGGGAGCCGCTGGCTCTACCATG<br>GGCGCTGCCTCTATCACCCTGACAGTGCAGGCCAGACAGCTGCTCAGCGGCATCGTGCAGCAGCAGAGC<br>AACCTGCTGAGAGCCATTGAGGCCCAGCAGCACATGCTGCAGCTGACCGTGTGGGGCATTAAGCAGCTC<br>CAGACACGGGTGCTGGCCATCGAGAGATACCTGCAGGATCAGCAGCTCCTGGGCCTGTGGGGCTGTAGC<br>GGCAAGCTGATCTGTACCACCGCCGTGCCCTGGAATACCTCTTGGAGCAACAAGAGCCAGACCGACATC<br>TGGGACAACATGACCTGGATGCAGTGGGACAAAGAAATCGGCAACTATACCGGCGAGATCTATAGACTG<br>CTGGAAGAGTCCCAGAACCAGCAGGAAAAGAACGAGAAGGACCTGCTGGCCCTGGATTCTTGGAACAAT<br>CTGTGGAACTGGTTCAGCATCTCCAAGTGGCTGTGGTACATCAAGATCTTCATCATGATCGTGGGCGGC<br>CTGATCGGCCTGCGCGATCATCTTTGCCGTGCTGAGCATCGTGAACCGCGTGCGGCAGGGCTAC |
| 11 | Mos1 GagPol (nucleic acid) | ATGGGAGCCAGAGCCAGCGTGCTGTCCGGAGGGGAGCTGGACCGCTGGGAGAAGATCAGGCTGAGGCCT<br>GGGAGGAAGAAGAAGTACAGGCTGAAGCACATCGTGTGGGCCAGCAGAGAGCTGGAACGGTTTGCCGTG<br>AACCCTGGCCTGCTGGAAACCAGCGAGGGCTGTAGGCAGATTCTGGGACAGCTGCAGCCCAGCCTGCAG<br>ACAGGCAGCGAGGAACTGCGGAGCCTGTACAACACCGTGGCCACCCTGTACTGCGTGCACCAGCGGATC<br>GAGATCAAGGACACCAAAGAAGCCCTGGAAAAGATCGAGGAAGAGCAGAACAAGAGCAAGAAGAAAGCC<br>CAGCAGGCTGCCGCTGACACAGGCAACAGCAGCCAGGTGTCCAGAACTACCCCATCGTGCAGAACATC<br>CAGGGACAGATGGTGCACCAGGCCATCAGCCCTCGGACCCTGAACGCCTGGGTGAAGGTGGTGGAGGAA<br>AAGGCCTTCAGCCCTGAGGTGATCCCCATGTTCTCTGCCCTGAGCGAGGGGAGCCACACCCCAGGACCTG<br>AACACCATGCTGAACACCGTGGGAGGGCACCAGGCTGCCATGCAGATGCTGAAAGAGACAATCAACGAG<br>GAAGCTGCCGAGTGGGACAGGGTCCACCCAGTGCACGCTGGACCTATCGCTCCTGGCCAGATGAGAGAG<br>CCCAGAGGCAGCGATATTGCTGGCACCACCTCCACACTGCAGGAACAGATCGGCTGGATGACCAACAAC<br>CCTCCCATCCCTGTGGGAGAGATCTACAAGCGGTGGATCATTCTGGGACTGAACAAGATCGTGCGGATG<br>TACAGCCCTGTGAGCATCCTGGACATCAGGCAGGGACCCAAAGAGCCCTTCAGGGACTACGTGGACCGG<br>TTCTACAAGACCCTGAGAGCCGAGCAGGCCAGCCAGGACGTGAAGAACTGGATGACCGAGACACTGCTG<br>GTGCAGAACGCCAACCCTGACTGCAAGACCATCCTGAAAGCCCTGGGACCTGCTGCCACCCTGGAAGAG<br>ATGATGACAGCCTGCCAGGGAGTGGGAGGACCTGGCCACAAGGCCAGGGTGCTGGCCGAGGCCATGAGC<br>CAGGTGACCAACTCTGCCACCATCATGATGCAGAGAGGCAACTTCCGGAACCAGAGAAAGACCGTGAAG<br>TGCTTCAACTGTGGCAAAGAGGGACACATTGCCAAGAACTGCAGGGCTCCCAGGAAGAAAGGCTGCTGG<br>AAGTGCGGAAAAGAAGGCCACCAGATGAAGGACTGCACCGAGAGACAGGCCAACTTCCTGGGCAAGATC<br>TGGCCTAGCAACAAGGGCAGGCCTGGCAACTTCCTGCAGAACAGACCCGAGCCCACCGCTCCTCCCGAG<br>GAAAGCTTCCGGTTTGGCGAGGAAACCACCACCCCTAGCCAGAAGCAGGAACCCATCGACAAAGAGATG<br>TACCCTCTGGCCAGCCTGAAGAGCCTGTTCGGCAACGACCCCAGCAGCCAGATGGCTCCCATCAGCCCA<br>ATCGAGACAGTGCCTGTGAAGCTGAAGCCTGGCATGGACGGACCCAGGGTGAAGCAGTGGCCTCTGACC<br>GAGGAAAAGATCAAAGCCCTGACAGCCATCTGCGAGGAAATGGAAAAAGAGGGCAAGATCACCAAGATC<br>GGACCCGAGAACCCCTACAACACCCCTGTGTTCGCCATCAAGAAGAAAGACAGCACCAAGTGGAGGAAA<br>CTGGTGGACTTCAGAGAGCTGAACAAGCGGACCCAGGACTTCTGGGAGGTGCAGCTGGGCATCCCTCAC<br>CCTGCTGGCCTGAAGAAAAGAAAGCGTGACCGTGCTGGCTGTGGGAGATGCCTACTTCAGCGTGCCT<br>CTGGACGAGGGCTTCCGGAAGTACACAGCCTTCACCATCCCCAGCACCAACAACGAGACACCTGGCATC<br>AGATACCAGTACAACGTGCTGCCTCAGGGCTGGAAAGGCAGCCCTGCCATCTTCCAGTGCAGCATGACC<br>AGAATCCTGGAACCCTTCAGAGCCAAGAACCCTGAGATCGTGATCTACCAGTATATGGCTGCCCTCTAC |

SEQUENCE LISTING

| SEQ ID NO: | Description | Sequence |
|---|---|---|
| | | GTGGGCAGCGACCTGGAAATCGGACAGCACAGAGCCAAAATCGAAGAACTCCGCGAGCACCTGCTGAAG<br>TGGGGATTCACCACCCCTGACAAGAAGCACCAGAAAGAGCCTCCCTTCCTGTGGATGGGCTACGAGCTG<br>CACCCTGACAAGTGGACCGTGCAGCCCATCCAGCTGCCAGAGAAGGACTCCTGGACCGTGAACGACATC<br>CAGAAACTGGTCGGCAAGCTGAACTGGGCCAGCCAGATCTACCCTGGCATCAAAGTCAGACAGCTGTGT<br>AAGCTGCTGAGGGGAGCCAAAGCACTGACCGACATCGTGCCTCTGACAGAAGAAGCCGAGCTGGAACTG<br>GCCGAGAACAGAGAGATCCTGAAAGAACCCGTGCACGGAGTGTACTACGACCCCTCCAAGGACCTGATT<br>GCCGAGATCCAGAAACAGGGACACGACCAGTGGACCTACCAGATCTATCAGGAACCTTTCAAGAACCTG<br>AAAACAGGCAAGTACGCCAAGATGCGGACAGCCCACACCAACGACGTGAAGCAGCTGACCGAAGCCGTG<br>CAGAAAATCGCCATGGAAAGCATCGTGATCTGGGGAAAGACACCCAAGTTCAGGCTGCCCATCCAGAAA<br>GAGACATGGGAAACCTGGTGGACCGACTACTGGCAGGCCACCTGGATTCCCGAGTGGGAGTTCGTGAAC<br>ACCCCACCCCTGGTGAAGCTGTGGTATCAGCTGGAAAAGGACCCTATCGCTGGCGTGGAGACATTCTAC<br>GTGGCTGGAGCTGCCAACAGAGAGACAAAGCTGGGCAAGGCTGGCTACGTGACCGACAGAGGCAGACAG<br>AAAATCGTGAGCCTGACCGAAACCACCAACCAGAAAACAGCCCYGCAGGCCATCTATCTGGCACTGCAG<br>GACAGCGGAAGCGAGGTGAACATCGTGACAGCCAGCCAGTATGCCCTGGGCATCATCCAGGCCCAGCCT<br>GACAAGAGCGAGAGCGAGCTGGTGAACCAGATCATCGAGCAGCTGATCAAGAAAGAACGGGTGTACCTG<br>AGCTGGGTGCCAGCCCACAAGGGCATCGGAGGGAACGAGCAGGTGGCCAAGCTGGTGTCCAGCGGAATC<br>CGGAAGGTGCTGTTCCTGGACGGCATCGATAAAGCCCAGGAAGAGCACGAGAAGTACCACAGCAATTGG<br>AGAGCCATGGCCAGCGACTTCAACCTGCCTCCCGTGGTGGCCAAAGAAATCGTGGCCAGCTGCGACCAG<br>TGCCAGCTGAAAGGCGAGGCCATGCACGGACAGGTGGACTGCTCCCCTGGCATCTGGCAGCTGGCATGC<br>ACCCACCTGGAAGGCAAGATCATTCTGGTGGCCGTGCACGTGGCCAGCGGATACATCGAAGCCGAAGTG<br>ATCCCTGCCGAGACAGGGCAGGAAACAGCCTACTTCATCCTGAAGCTGGCTGGCAGATGGCCTGTGAAG<br>GTGATCCACACAGCCAACGGCAGCAACTTCACCTCTGCTGCCGTGAAGGCTGCCTGTTGGTGGGCTGGC<br>ATTCAGCAGGAATTTGGCATCCCCTACAATCCCCAGTCTCAGGGAGTGGTGGCCAGCATGAACAAAGAG<br>CTGAAGAAGATCATCGGACAGGTCAGGGATCAGGCCGAGCACCTGAAAACTGCCGTCCAGATGGCCGTG<br>TTCATCCACAACTTCAAGCGGAAGGGAGGGATCGGAGGGTACTCTGCTGGCGAGCGGATCATCGACATC<br>ATTGCCACCGATATCCAGACCAAAGAGCTGCAGAAACAGATCATCAAGATCCAGAACTTCAGGGTGTAC<br>TACAGGGACAGCAGGGACCCCATCTGGAAGGGACCTGCCAAGCTGCTGTGGAAAGGCGAAGGAGCCGTC<br>GTCATCCAGGACAACAGCGACATCAAGGTGGTGCCCAGACGGAAGGTGAAAATCATCAAGGACTACGGC<br>AAACAGATGGCTGGAGCCGACTGTGTCGCTGGCAGGCAGGACGAGGAC |
| 12 | Mos2 GagPol (nucleic acid) | ATGGGAGCCAGAGCCAGCATCCTGCGAGGAGGGAAGCTGGACAAGTGGGAGAAGATCAGGCTGAGGCCT<br>GGAGGGAAGAAACACTACATGCTGAAGCACCTGGTCTGGGCCAGCAGAGAGCTGGAACGGTTTGCCCTC<br>AATCCTGGCCTGCTGGAAACCAGCGAGGGCTGCAAGCAGATCATCAAGCAGCTGCAGCCTGCCCTGCAG<br>ACAGGCACCGAGGAACTGCGGAGCCTGTTCAACACCGTGGCCACCCTGTACTGCGTGCATGCCGAGATC<br>GAAGTGAGGGACACCAAAGAAGCCCTGGACAAGATCGAGGAAGAGCAGAACAAGAGCCAGCAGAAACC<br>CAGCAGGCCAAAGAAGCCGACGGCAAGGTCTCCCAGAACTACCCCATCGTGCAGAACCTGCAGGGACAG<br>ATGGTGCACCAGCCCATCAGCCCTCGGACACTGAATGCCTGGGTGAAGGTGATCGAGGAAAAGGCCTTC<br>AGCCCTGAGGTGATCCCCATGTTCACAGCCCTGAGCGAGGGAGCCACACCCCAGGACCTGAACACCATG<br>CTGAACACCGTGGGAGGGCACCAGGCTGCCSTGCAGATGCTGAAGGACACCATCAACGAGGAAGCTGCC<br>GAGTGGGACAGGCTGCACCCTGTGCACGCTGGACCTGTGGCTCCTGGCCAGATGAGAGAGCCCAGAGGC<br>AGCGATATTGCTGGCACCACCTCCAATCTGCAGGAACAGATCGCCTGGATGACCAGCAACCCTCCCATC<br>CCTGTGGGAGACATCTACAAGCGGTGGATCATCCTGGGACTGAACAAGATCGTGCGGATGTACAGCCCT<br>ACCTCCATCCTGGACATCAAGCAGGGACCCAAAGAGCCTTTCAGGGACTACGTGGACCGGTTCTTCAAG<br>ACCCTGAGAGCCGAGCAGGCCACCCAGGACGTGAAGAACTGGATGACCGACACCCTGCTGGTGCAGAAC<br>GCCAACCCTGACTGCAAGACCATCCTGAGAGCCCTGGGACCTGGAGCCACCCTGGAAGAGATGATGACA<br>GCCTGCCAGGGAGTGGGAGGACCCTCTCACAAGGCTAGGGTGCTGGCCGAGGCCATGAGCCAGACCAAC<br>AGCACCATCCTGATGCAGCGGAGCAACTTCAAGGGCAGCAAGCGGATCGTGAAGTGCTTCAACTGTGGC<br>AAAGAGGGACACATTGCCAGAAACTGTAGGGCACCCAGGAAGAAAGGCTGCTGGAAGTGCGGAAAAGAA<br>GGCCACCAGATGAAGGACTGCACCGAGAGGCAGGCCAACTTCCTGGGCAAGATCTGGCCTAGCCACAAG<br>GGCAGACCTGGCAACTTCCTGCAGAGCAGACCCGAGCCCACCGCTCCTCCAGCCGAGAGCTTCCGGTTC<br>GAGGAAACCACCCCTGCTCCCAAGCAGGAACCTAAGGACAGAGAGCCTCTGACCAGCCTGAGAAGCCTG<br>TTCGGCAGCGACCCTCTGAGCCAGATGGCTCCCATCTCCCCTATCGAGACAGTGCCTGTGAAGCTGAAG<br>CCTGGCATGGACGGACCCAAGGTGAAACAGTGGCCTCTGACCGAGGAAAAGATCAAAGCCCTGGTGGAG<br>ATCTGTACCGAGATGGAAAAAGAGGGCAAGATCAGCAAGATCGGACCCGAGAACCCCTACAACACCCCT<br>ATCTTCGCCATCAAGAAGAAAGACAGCACCAAGTGGAGGAAACTGGTGGACTTCAGAGAGCTGAACAAG<br>CGGACCCAGGACTTCTGGGAGGTGCAGCTGGGCATCCCTCACCCTGCTGGCCTGAAGAAAAAGAAAGC<br>GTGACCGTGCTGGCCGTGGGAGATGCCTACTTCAGCAGTGCCTCTGGACGAGGACTTCAGAAAGTACACA<br>GCCTTCACCATCCCCAGCATCAACAACGAGACACCTGGCATCAGATACCAGTACAACGTGCTGCCTCAG<br>GGATGGAAGGGCTCTCCTGCAATCTTCCAGAGCAGCATGACCAAGATCCTGGAACCCTTCCGGAAGCAG<br>AACCCTGACATCGTGATCTACCAGTACATGGCAGCCCTGTACGTCGGCAGCGACCTGGAAATCGGACAG<br>CACCGGACCAAGATCGAAGAACTCAGGCAGCACCTGCTGCGGTGGGGATTCACCACCCCTGACAAGAAG<br>CACCAGAAAGAGCCTCCCTTCCTGTGGATGGGCTACGAGCTGCACCCAGACAAGTGGACCGTGCAGCCC<br>ATCGTGCTGCCTGAGAAGGACTCCTGGACCGTGAACGACATCCAGAAACTGGTCGGCAAGCTGAACTGG<br>GCCAGCCAGATCTACGCTGGCATCAAAGTGAAGCAGCTGTGTAAGCTCCTGAGAGGCACCAAAGCCCTG<br>ACCGAGGTGGTGCCACTGACAGAGGAAGCCGAGCTGGAACTGGCCGAGAACAGAGAGATCCTGAAAGAA<br>CCCGTGCACGGAGTGTACTACGACCCCAGCAAGGACCTGATTGCCGAGATCCAGAAGCAGGGACAGGGA<br>CAGTGGACCTACCAGATCTACCAGGAACCTTCAAGAACCTGAAAACCGGCAAGTACGCCAGGATGAGG<br>GGAGCCCACACCAACGACGTCAAACAGCTGACCGAAGCCGTGCAGAAGATCGCCACCGAGAGCATCGTG<br>ATTTGGGGAAAGACACCCAAGTTCAAGCTGCCCATCCAGAAAGAGACATGGGAGGCCTGGTGGACCGAG<br>TACTGGCAGGCCACCTGGATTCCCGAGTGGGAGTTCGTGAACACCCCACCCCTGGTGAAGCTGTGGTAT<br>CAGCTGGAAAAGAACCCATCGTGGGAGCCGAGACATTCTACGTGGCTGGAGCTGCCAACAGAGAGACA<br>AAGCTGGGCAAGGCTGGCTACGTGACCGACAGAGGCAGGCAGAAAGTGGTGTCCCTGACCGATACCACC<br>AACCAGAAAACAGCCCTGCAGGCCATCCACCTGGCTCTGCAGGACTCTGGCCTGGAAGTGAACATCGTG |

SEQUENCE LISTING

| SEQ ID NO: | Description | Sequence |
|---|---|---|
| | | ACAGCCAGCCAGTATGCCCTGGGCATCATTCAGGCACAGCCTGACAAGAGCGAGAGCGAGCTGGTGTCT<br>CAGATCATTGAGCAGCTGATCAAGAAAGAAAAGGTGTACCTGGCCTGGGTGCCAGCCCACAAGGGGATC<br>GGAGGGAACGAGCAGGTGGACAAGCTGGTGTCCAGGGGCATCCGGAAGGTGCTGTTTCTGGACGGCATC<br>GACAAAGCCCAGGAAGAGCACGAGAAGTACCACAGCAATTGGAGAGCCATGGCCAGCGAGTTCAACCTG<br>CCTCCCATCGTGGCCAAAGAAATCGTGGCCTCTTGCGACAAGTGCCAGCTGAAAGGCGAGGCCATTCAC<br>GGACAGGTGGACTGCAGCCCAGGCATCTGGCAGCTGGCCTGCACCCACCTGGAAGGCAAGGTGATCCTG<br>GTGGCCGTGCACGTGGCCTCTGGATACATCGAAGCCGAAGTGATCCCTGCCGAGACAGGCCAGGAAACA<br>GCCTACTTCCTGCTGAAGCTGGCTGGCAGGTGGCCTGTGAAAACCATCCACACAGCCAACGGCAGCAAC<br>TTCACCTCTGCCACCGTGAAGGCTGCCTGTTGGTGGGCTGGCATTAAGCAGGAATTTGGCATCCCCTAC<br>AACCCTCAGTCTCAGGGAGTGGTGGCCTCCATCAACAAAGAGCTGAAGAAGATCATCGGACAGGTCAGG<br>GATCAGGCCGAGCATCTGAAAACAGCCGTCCAGATGGCCGTGTTCATCCACAACTTCAAGCGGAAGGGA<br>GGGATCGGAGAGTACTCTGCTGGCGAGAGGATCGTGGACATTATCGCCAGCGATATCCAGACCAAAGAA<br>CTGCAGAAGCAGATCACAAAGATCCAGAACTTCAGGGTGTACTACAGGGACAGCAGAGATCCCCTGTGG<br>AAGGGACCTGCCAAGCTGCTGTGGAAAGGCGAAGGAGCCGTGGTCATCCAGGACAACAGCGACATCAAG<br>GTGGTGCCCAGACGGAAGGCCAAGATCATCAGAGACTACGGCAAACAGATGGCTGGCGACGACTGCGTC<br>GCCTCTAGGCAGGACGAGGAC |

The invention claimed is:

1. A method of inducing an immune response against a human immunodeficiency virus (HIV) in a subject, the method comprising co-locally administering to the subject:
   a. an immunogenically effective amount of an isolated HIV envelope (Env) polypeptide; and
   b. an immunogenically effective amount of an adenovirus vector encoding an HIV Env antigen,
   wherein the immunogenically effective amount of the isolated HIV Env polypeptide and the immunogenically effective amount of the adenovirus vector are co-locally administered in separate compositions as intramuscular injections using two separate syringes to the same muscle and wherein the injections are within 10 cm of each other, and wherein the compositions do not comprise an adjuvant.

2. The method of claim 1, wherein the immunogenically effective amount of the isolated HIV Env polypeptide and the immunogenically effective amount of the adenovirus vector are administered co-locally for boosting immunization after administering to the subject an immunogenically effective amount of an adenovirus vector encoding an HIV Env antigen.

3. The method of claim 1, wherein the adenovirus vector is an adenovirus 26 (rAd26) vector.

4. The method of claim 1, further comprising administering an immunogenically effective amount of a second adenovirus vector encoding a second HIV Env antigen together with the immunogenically effective amount of the adenovirus vector.

5. The method of claim 4, wherein the second adenovirus vector is an adenovirus 26 (rAd26) vector.

6. A method of inducing an immune response against a human immunodeficiency virus (HIV) in a subject, the method comprising co-locally administering to the subject:
   a. an immunogenically effective amount of an isolated HIV envelope (Env) polypeptide; and
   b. an immunogenically effective amount of an adenovirus vector encoding an HIV Env antigen,
   wherein the immunogenically effective amount of the isolated HIV Env polypeptide and the immunogenically effective amount of the adenovirus vector are co-locally administered in separate compositions as intramuscular injections using two separate syringes to the same muscle and wherein the injections are within 10 cm of each other, and wherein the compositions do not comprise an adjuvant that is or comprises any one of aluminum phosphate, aluminum hydroxide, aluminum sulfate, aluminum oxide, calcium phosphate, liposomes, oil-in-water emulsion, water-in-oil emulsion, paraffin oil, toxoids, saponins or fractions thereof, IL-1, IL-2, IL-12, MoGM-CSF, lipid A or analogs or derivatives thereof, CpG, or imidazoquinolines, or any combination thereof.

7. The method of claim 6, wherein the immunogenically effective amount of the isolated HIV Env polypeptide and the immunogenically effective amount of the adenovirus vector are administered co-locally for boosting immunization after administering to the subject an immunogenically effective amount of an adenovirus vector encoding an HIV Env antigen.

8. The method of claim 6, wherein the adenovirus vector is an adenovirus 26 (rAd26) vector.

9. The method of claim 6, further comprising administering an immunogenically effective amount of a second adenovirus vector encoding a second HIV Env antigen together with the immunogenically effective amount of the adenovirus vector.

10. The method of claim 9, wherein the second adenovirus vector is an adenovirus 26 (rAd26) vector.

11. The method of claim 6, wherein the compositions do not comprise any adjuvant.

12. The method of claim 1, further comprising administering an immunogenically effective amount of one or more adenovirus vectors encoding further HIV antigens to which an immune response is induced in the subject.

13. The method of claim 1, wherein the immune response comprises a T-helper 1 (Th1) biased immune response.

14. The method of claim 6, further comprising administering an immunogenically effective amount of one or more adenovirus vectors encoding further HIV antigens to which an immune response is induced in the subject.

15. The method of claim 6, wherein the immune response comprises a T-helper 1 (Th1) biased immune response.

* * * * *

SEQUENCE LISTING

<160> NUMBER OF SEQ ID NOS: 12

<210> SEQ ID NO 1
<211> LENGTH: 685
<212> TYPE: PRT
<213> ORGANISM: Artificial Sequence
<220> FEATURE:
<223> OTHER INFORMATION: Mos1Env

<400> SEQUENCE: 1

```
Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
    130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205
```

```
Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
            275                 280                 285

Ile Met Val Gln Leu Asn Val Ser Val Glu Ile Asn Cys Thr Arg Pro
290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
            355                 360                 365

Ser Gly Gly Asp Pro Glu Ile Val Met His Ser Phe Asn Cys Gly Gly
370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
            435                 440                 445

Arg Cys Ser Ser Asn Ile Thr Gly Leu Leu Leu Thr Arg Asp Gly Gly
450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
            500                 505                 510

Ser Glu Lys Ser Ala Val Gly Ile Gly Ala Val Phe Leu Gly Phe Leu
            515                 520                 525

Gly Ala Ala Gly Ser Thr Met Gly Ala Ala Ser Met Thr Leu Thr Val
530                 535                 540

Gln Ala Arg Leu Leu Leu Ser Gly Ile Val Gln Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
            595                 600                 605

Cys Thr Thr Thr Val Pro Trp Asn Ala Ser Trp Ser Asn Lys Ser Leu
610                 615                 620
```

```
Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
                645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp
        675                 680                 685

<210> SEQ ID NO 2
<211> LENGTH: 684
<212> TYPE: PRT
<213> ORGANISM: Artificial Sequence
<220> FEATURE:
<223> OTHER INFORMATION: Mos2Env

<400> SEQUENCE: 2

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
            100                 105                 110

Gln Ser Leu Lys Pro Cys Val Lys Leu Thr Pro Leu Cys Val Thr Leu
        115                 120                 125

Glu Cys Arg Asn Val Arg Asn Val Ser Ser Asn Gly Thr Tyr Asn Ile
    130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Ser Thr Gln Leu Leu Leu Asn Gly
            260                 265                 270

Ser Leu Ala Glu Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300
```

Cys Thr Arg Pro Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
            325                 330                 335

Ala His Cys Asn Leu Ser Arg Asp Gly Trp Asn Lys Thr Leu Gln Gly
            340                 345                 350

Val Lys Lys Leu Ala Glu His Phe Pro Asn Lys Thr Ile Asn Phe
            355                 360                 365

Thr Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
            405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
            435                 440                 445

Asn Ile Thr Gly Leu Leu Leu Thr Arg Asp Gly Gly Ser Asn Asn Gly
            450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
            485                 490                 495

Pro Leu Gly Val Ala Pro Thr Glu Ala Lys Arg Arg Val Val Glu Ser
            500                 505                 510

Glu Lys Ser Ala Val Gly Ile Gly Ala Val Phe Leu Gly Ile Leu Gly
            515                 520                 525

Ala Ala Gly Ser Thr Met Gly Ala Ala Ser Ile Thr Leu Thr Val Gln
            530                 535                 540

Ala Arg Gln Leu Leu Ser Gly Ile Val Gln Gln Gln Ser Asn Leu Leu
545                 550                 555                 560

Arg Ala Ile Glu Ala Gln Gln His Met Leu Gln Leu Thr Val Trp Gly
            565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
            595                 600                 605

Thr Thr Ala Val Pro Trp Asn Thr Ser Trp Ser Asn Lys Ser Gln Thr
            610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
            645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp
            675                 680

<210> SEQ ID NO 3
<211> LENGTH: 711
<212> TYPE: PRT
<213> ORGANISM: Artificial Sequence
<220> FEATURE:

<223> OTHER INFORMATION: Mos2SEnv

<400> SEQUENCE: 3

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val Met Gly Asn
            20                  25                  30

Leu Trp Val Thr Val Tyr Tyr Gly Val Pro Val Trp Lys Asp Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Ala Ser Leu Glu Pro Cys Val Lys Leu Thr Pro Leu Cys Val Thr Leu
        115                 120                 125

Asn Cys Arg Asn Val Arg Asn Val Ser Ser Asn Gly Thr Tyr Asn Ile
130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Lys Phe
        355                 360                 365

Ala Pro His Ser Gly Gly Asp Leu Glu Ile Thr Thr His Thr Phe Asn
    370                 375                 380

Cys Arg Gly Glu Phe Phe Tyr Cys Asn Thr Ser Asn Leu Phe Asn Glu
385                 390                 395                 400

```
Ser Asn Ile Glu Arg Asn Asp Ser Ile Ile Thr Leu Pro Cys Arg Ile
                405                 410                 415

Lys Gln Ile Ile Asn Met Trp Gln Glu Val Gly Arg Ala Ile Tyr Ala
            420                 425                 430

Pro Pro Ile Ala Gly Asn Ile Thr Cys Arg Ser Asn Ile Thr Gly Leu
        435                 440                 445

Leu Leu Thr Arg Asp Gly Gly Ser Asn Asn Gly Val Pro Asn Asp Thr
    450                 455                 460

Glu Thr Phe Arg Pro Gly Gly Gly Asp Met Arg Asn Asn Trp Arg Ser
465                 470                 475                 480

Glu Leu Tyr Lys Tyr Lys Val Val Glu Val Lys Pro Leu Gly Val Ala
                485                 490                 495

Pro Thr Glu Ala Lys Arg Arg Val Val Glu Arg Glu Lys Arg Ala Val
            500                 505                 510

Gly Ile Gly Ala Val Phe Leu Gly Ile Leu Gly Ala Ala Gly Ser Thr
        515                 520                 525

Met Gly Ala Ala Ser Ile Thr Leu Thr Val Gln Ala Arg Gln Leu Leu
    530                 535                 540

Ser Gly Ile Val Gln Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
                565                 570                 575

Thr Arg Val Leu Ala Ile Glu Arg Tyr Leu Gln Asp Gln Gln Leu Leu
            580                 585                 590

Gly Leu Trp Gly Cys Ser Gly Lys Leu Ile Cys Thr Thr Ala Val Pro
    595                 600                 605

Trp Asn Thr Ser Trp Ser Asn Lys Ser Gln Thr Asp Ile Trp Asp Asn
    610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Gln Glu Lys Asn Glu
                645                 650                 655

Lys Asp Leu Leu Ala Leu Asp Ser Trp Asn Asn Leu Trp Asn Trp Phe
            660                 665                 670

Ser Ile Ser Lys Trp Leu Trp Tyr Ile Lys Ile Phe Ile Met Ile Val
        675                 680                 685

Gly Gly Leu Ile Gly Leu Arg Ile Ile Phe Ala Val Leu Ser Ile Val
    690                 695                 700

Asn Arg Val Arg Gln Gly Tyr
705                 710

<210> SEQ ID NO 4
<211> LENGTH: 1350
<212> TYPE: PRT
<213> ORGANISM: Artificial Sequence
<220> FEATURE:
<223> OTHER INFORMATION: Mos1GagPol

<400> SEQUENCE: 4

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45
```

```
Gly Leu Leu Glu Thr Ser Glu Gly Cys Arg Gln Ile Leu Gly Gln Leu
 50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Glu Lys Ile Glu Glu Glu Gln Asn Lys Ser Lys
                100                 105                 110

Lys Lys Ala Gln Gln Ala Ala Ala Asp Thr Gly Asn Ser Ser Gln Val
                115                 120                 125

Ser Gln Asn Tyr Pro Ile Val Gln Asn Ile Gln Gly Gln Met Val His
            130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
        435                 440                 445

Leu Gln Asn Arg Pro Glu Pro Thr Ala Pro Pro Glu Glu Ser Phe Arg
    450                 455                 460
```

```
Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
            485                 490                 495

Pro Ser Ser Gln Met Ala Pro Ile Ser Pro Ile Glu Thr Val Pro Val
        500                 505                 510

Lys Leu Lys Pro Gly Met Asp Gly Pro Arg Val Lys Gln Trp Pro Leu
    515                 520                 525

Thr Glu Glu Lys Ile Lys Ala Leu Thr Ala Ile Cys Glu Glu Met Glu
530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
        595                 600                 605

Thr Val Leu Ala Val Gly Asp Ala Tyr Phe Ser Val Pro Leu Asp Glu
    610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
            660                 665                 670

Phe Arg Ala Lys Asn Pro Glu Ile Val Ile Tyr Gln Tyr Met Ala Ala
        675                 680                 685

Leu Tyr Val Gly Ser Asp Leu Glu Ile Gly Gln His Arg Ala Lys Ile
    690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
        755                 760                 765

Ala Ser Gln Ile Tyr Pro Gly Ile Lys Val Arg Gln Leu Cys Lys Leu
    770                 775                 780

Leu Arg Gly Ala Lys Ala Leu Thr Asp Ile Val Pro Leu Thr Glu Glu
785                 790                 795                 800

Ala Glu Leu Glu Leu Ala Glu Asn Arg Glu Ile Leu Lys Glu Pro Val
                805                 810                 815

His Gly Val Tyr Tyr Asp Pro Ser Lys Asp Leu Ile Ala Glu Ile Gln
            820                 825                 830

Lys Gln Gly His Asp Gln Trp Thr Tyr Gln Ile Tyr Gln Glu Pro Phe
        835                 840                 845

Lys Asn Leu Lys Thr Gly Lys Tyr Ala Lys Met Arg Thr Ala His Thr
    850                 855                 860

Asn Asp Val Lys Gln Leu Thr Glu Ala Val Gln Lys Ile Ala Met Glu
865                 870                 875                 880
```

-continued

```
Ser Ile Val Ile Trp Gly Lys Thr Pro Lys Phe Arg Leu Pro Ile Gln
                885                 890                 895
Lys Glu Thr Trp Glu Thr Trp Trp Thr Asp Tyr Trp Gln Ala Thr Trp
            900                 905                 910
Ile Pro Glu Trp Glu Phe Val Asn Thr Pro Leu Val Lys Leu Trp
        915                 920                 925
Tyr Gln Leu Glu Lys Asp Pro Ile Ala Gly Val Glu Thr Phe Tyr Val
    930                 935                 940
Ala Gly Ala Ala Asn Arg Glu Thr Lys Leu Gly Lys Ala Gly Tyr Val
945                 950                 955                 960
Thr Asp Arg Gly Arg Gln Lys Ile Val Ser Leu Thr Glu Thr Thr Asn
                965                 970                 975
Gln Lys Thr Ala Leu Gln Ala Ile Tyr Leu Ala Leu Gln Asp Ser Gly
            980                 985                 990
Ser Glu Val Asn Ile Val Thr Ala Ser Gln Tyr Ala Leu Gly Ile Ile
        995                 1000                1005
Gln Ala Gln Pro Asp Lys Ser Glu Ser Glu Leu Val Asn Gln Ile
    1010                1015                1020
Ile Glu Gln Leu Ile Lys Lys Glu Arg Val Tyr Leu Ser Trp Val
    1025                1030                1035
Pro Ala His Lys Gly Ile Gly Gly Asn Glu Gln Val Asp Lys Leu
    1040                1045                1050
Val Ser Ser Gly Ile Arg Lys Val Leu Phe Leu Asp Gly Ile Asp
    1055                1060                1065
Lys Ala Gln Glu Glu His Glu Lys Tyr His Ser Asn Trp Arg Ala
    1070                1075                1080
Met Ala Ser Asp Phe Asn Leu Pro Pro Val Val Ala Lys Glu Ile
    1085                1090                1095
Val Ala Ser Cys Asp Gln Cys Gln Leu Lys Gly Glu Ala Met His
    1100                1105                1110
Gly Gln Val Asp Cys Ser Pro Gly Ile Trp Gln Leu Ala Cys Thr
    1115                1120                1125
His Leu Glu Gly Lys Ile Ile Leu Val Ala Val His Val Ala Ser
    1130                1135                1140
Gly Tyr Ile Glu Ala Glu Val Ile Pro Ala Glu Thr Gly Gln Glu
    1145                1150                1155
Thr Ala Tyr Phe Ile Leu Lys Leu Ala Gly Arg Trp Pro Val Lys
    1160                1165                1170
Val Ile His Thr Ala Asn Gly Ser Asn Phe Thr Ser Ala Ala Val
    1175                1180                1185
Lys Ala Ala Cys Trp Trp Ala Gly Ile Gln Gln Glu Phe Gly Ile
    1190                1195                1200
Pro Tyr Asn Pro Gln Ser Gln Gly Val Val Ala Ser Met Asn Lys
    1205                1210                1215
Glu Leu Lys Lys Ile Ile Gly Gln Val Arg Asp Gln Ala Glu His
    1220                1225                1230
Leu Lys Thr Ala Val Gln Met Ala Val Phe Ile His Asn Phe Lys
    1235                1240                1245
Arg Lys Gly Gly Ile Gly Gly Tyr Ser Ala Gly Glu Arg Ile Ile
    1250                1255                1260
Asp Ile Ile Ala Thr Asp Ile Gln Thr Lys Glu Leu Gln Lys Gln
    1265                1270                1275
```

```
Ile Ile Lys Ile Gln Asn Phe Arg Val Tyr Tyr Arg Asp Ser Arg
    1280                1285                1290

Asp Pro Ile Trp Lys Gly Pro Ala Lys Leu Leu Trp Lys Gly Glu
    1295                1300                1305

Gly Ala Val Val Ile Gln Asp Asn Ser Asp Ile Lys Val Val Pro
    1310                1315                1320

Arg Arg Lys Val Lys Ile Ile Lys Asp Tyr Gly Lys Gln Met Ala
    1325                1330                1335

Gly Ala Asp Cys Val Ala Gly Arg Gln Asp Glu Asp
    1340                1345                1350

<210> SEQ ID NO 5
<211> LENGTH: 1341
<212> TYPE: PRT
<213> ORGANISM: Artificial Sequence
<220> FEATURE:
<223> OTHER INFORMATION: Mos2GagPol

<400> SEQUENCE: 5

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285
```

```
Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
                355                 360                 365

Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
                420                 425                 430

Trp Pro Ser His Lys Gly Arg Pro Gly Asn Phe Leu Gln Ser Arg Pro
    435                 440                 445

Glu Pro Thr Ala Pro Pro Ala Glu Ser Phe Arg Phe Glu Glu Thr Thr
450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
                500                 505                 510

Lys Val Lys Gln Trp Pro Leu Thr Glu Glu Lys Ile Lys Ala Leu Val
    515                 520                 525

Glu Ile Cys Thr Glu Met Glu Lys Glu Gly Lys Ile Ser Lys Ile Gly
    530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
                580                 585                 590

Leu Lys Lys Lys Lys Ser Val Thr Val Leu Ala Val Gly Asp Ala Tyr
    595                 600                 605

Phe Ser Val Pro Leu Asp Glu Asp Phe Arg Lys Tyr Thr Ala Phe Thr
    610                 615                 620

Ile Pro Ser Ile Asn Asn Glu Thr Pro Gly Ile Arg Tyr Gln Tyr Asn
625                 630                 635                 640

Val Leu Pro Gln Gly Trp Lys Gly Ser Pro Ala Ile Phe Gln Ser Ser
                645                 650                 655

Met Thr Lys Ile Leu Glu Pro Phe Arg Lys Gln Asn Pro Asp Ile Val
                660                 665                 670

Ile Tyr Gln Tyr Met Ala Ala Leu Tyr Val Gly Ser Asp Leu Glu Ile
    675                 680                 685

Gly Gln His Arg Thr Lys Ile Glu Glu Leu Arg Gln His Leu Leu Arg
    690                 695                 700
```

-continued

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
            725                 730                 735

Ile Val Leu Pro Glu Lys Asp Ser Trp Thr Val Asn Asp Ile Gln Lys
        740                 745                 750

Leu Val Gly Lys Leu Asn Trp Ala Ser Gln Ile Tyr Ala Gly Ile Lys
    755                 760                 765

Val Lys Gln Leu Cys Lys Leu Arg Gly Thr Lys Ala Leu Thr Glu
770                 775                 780

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
                805                 810                 815

Asp Leu Ile Ala Glu Ile Gln Lys Gln Gly Gln Gly Gln Trp Thr Tyr
            820                 825                 830

Gln Ile Tyr Gln Glu Pro Phe Lys Asn Leu Lys Thr Gly Lys Tyr Ala
        835                 840                 845

Arg Met Arg Gly Ala His Thr Asn Asp Val Lys Gln Leu Thr Glu Ala
    850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                885                 890                 895

Glu Tyr Trp Gln Ala Thr Trp Ile Pro Glu Trp Glu Phe Val Asn Thr
            900                 905                 910

Pro Pro Leu Val Lys Leu Trp Tyr Gln Leu Glu Lys Glu Pro Ile Val
        915                 920                 925

Gly Ala Glu Thr Phe Tyr Val Ala Gly Ala Ala Asn Arg Glu Thr Lys
    930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                965                 970                 975

Leu Ala Leu Gln Asp Ser Gly Leu Glu Val Asn Ile Val Thr Ala Ser
            980                 985                 990

Gln Tyr Ala Leu Gly Ile Ile Gln Ala Gln Pro Asp Lys Ser Glu Ser
        995                 1000                1005

Glu Leu Val Ser Gln Ile Ile Glu Gln Leu Ile Lys Lys Glu Lys
    1010                1015                1020

Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
    1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110

Trp Gln Leu Ala Cys Thr His Leu Glu Gly Lys Val Ile Leu Val
    1115            1120                1125

Ala Val His Val Ala Ser Gly Tyr Ile Glu Ala Glu Val Ile Pro
    1130            1135                1140

Ala Glu Thr Gly Gln Glu Thr Ala Tyr Phe Leu Leu Lys Leu Ala
    1145            1150                1155

Gly Arg Trp Pro Val Lys Thr Ile His Thr Ala Asn Gly Ser Asn
    1160            1165                1170

Phe Thr Ser Ala Thr Val Lys Ala Ala Cys Trp Trp Ala Gly Ile
    1175            1180                1185

Lys Gln Glu Phe Gly Ile Pro Tyr Asn Pro Gln Ser Gln Gly Val
    1190            1195                1200

Val Ala Ser Ile Asn Lys Glu Leu Lys Lys Ile Ile Gly Gln Val
    1205            1210                1215

Arg Asp Gln Ala Glu His Leu Lys Thr Ala Val Gln Met Ala Val
    1220            1225                1230

Phe Ile His Asn Phe Lys Arg Lys Gly Gly Ile Gly Glu Tyr Ser
    1235            1240                1245

Ala Gly Glu Arg Ile Val Asp Ile Ile Ala Ser Asp Ile Gln Thr
    1250            1255                1260

Lys Glu Leu Gln Lys Gln Ile Thr Lys Ile Gln Asn Phe Arg Val
    1265            1270                1275

Tyr Tyr Arg Asp Ser Arg Asp Pro Leu Trp Lys Gly Pro Ala Lys
    1280            1285                1290

Leu Leu Trp Lys Gly Glu Gly Ala Val Val Ile Gln Asp Asn Ser
    1295            1300                1305

Asp Ile Lys Val Val Pro Arg Arg Lys Ala Lys Ile Ile Arg Asp
    1310            1315                1320

Tyr Gly Lys Gln Met Ala Gly Asp Asp Cys Val Ala Ser Arg Gln
    1325            1330                1335

Asp Glu Asp
    1340

<210> SEQ ID NO 6
<211> LENGTH: 679
<212> TYPE: PRT
<213> ORGANISM: Artificial Sequence
<220> FEATURE:
<223> OTHER INFORMATION: Clade C gp140

<400> SEQUENCE: 6

Ala Glu Asn Leu Trp Val Gly Asn Met Trp Val Thr Val Tyr Tyr Gly
1               5                   10                  15

Val Pro Val Trp Thr Asp Ala Lys Thr Thr Leu Phe Cys Ala Ser Asp
            20                  25                  30

Thr Lys Ala Tyr Asp Arg Glu Val His Asn Val Trp Ala Thr His Ala
        35                  40                  45

Cys Val Pro Thr Asp Pro Asn Pro Gln Glu Ile Val Leu Glu Asn Val
    50                  55                  60

Thr Glu Asn Phe Asn Met Trp Lys Asn Asp Met Val Asp Gln Met His
65                  70                  75                  80

Glu Asp Ile Ile Ser Leu Trp Asp Gln Ser Leu Lys Pro Cys Val Lys
                85                  90                  95

Leu Thr Pro Leu Cys Val Thr Leu His Cys Thr Asn Ala Thr Phe Lys
            100                 105                 110

-continued

```
Asn Asn Val Thr Asn Asp Met Asn Lys Glu Ile Arg Asn Cys Ser Phe
            115                 120                 125

Asn Thr Thr Thr Glu Ile Arg Asp Lys Lys Gln Gln Gly Tyr Ala Leu
        130                 135                 140

Phe Tyr Arg Pro Asp Ile Val Leu Leu Lys Glu Asn Arg Asn Asn Ser
145                 150                 155                 160

Asn Asn Ser Glu Tyr Ile Leu Ile Asn Cys Asn Ala Ser Thr Ile Thr
                165                 170                 175

Gln Ala Cys Pro Lys Val Asn Phe Asp Pro Ile Pro Ile His Tyr Cys
            180                 185                 190

Ala Pro Ala Gly Tyr Ala Ile Leu Lys Cys Asn Asn Lys Thr Phe Ser
        195                 200                 205

Gly Lys Gly Pro Cys Asn Asn Val Ser Thr Val Gln Cys Thr His Gly
    210                 215                 220

Ile Lys Pro Val Val Ser Thr Gln Leu Leu Leu Asn Gly Ser Leu Ala
225                 230                 235                 240

Glu Lys Glu Ile Ile Ile Arg Ser Glu Asn Leu Thr Asp Asn Val Lys
                245                 250                 255

Thr Ile Ile Val His Leu Asn Lys Ser Val Glu Ile Val Cys Thr Arg
            260                 265                 270

Pro Asn Asn Asn Thr Arg Lys Ser Met Arg Ile Gly Pro Gly Gln Thr
        275                 280                 285

Phe Tyr Ala Thr Gly Asp Ile Ile Gly Asp Ile Arg Gln Ala Tyr Cys
290                 295                 300

Asn Ile Ser Gly Ser Lys Trp Asn Glu Thr Leu Lys Arg Val Lys Glu
305                 310                 315                 320

Lys Leu Gln Glu Asn Tyr Asn Asn Lys Thr Ile Lys Phe Ala Pro
                325                 330                 335

Ser Ser Gly Gly Asp Leu Glu Ile Thr Thr His Ser Phe Asn Cys Arg
            340                 345                 350

Gly Glu Phe Phe Tyr Cys Asn Thr Thr Arg Leu Phe Asn Asn Asn Ala
        355                 360                 365

Thr Glu Asp Glu Thr Ile Thr Leu Pro Cys Arg Ile Lys Gln Ile Ile
    370                 375                 380

Asn Met Trp Gln Gly Val Gly Arg Ala Met Tyr Ala Pro Pro Ile Ala
385                 390                 395                 400

Gly Asn Ile Thr Cys Lys Ser Asn Ile Thr Gly Leu Leu Leu Val Arg
                405                 410                 415

Asp Gly Gly Glu Asp Asn Lys Thr Glu Glu Ile Phe Arg Pro Gly Gly
            420                 425                 430

Gly Asn Met Lys Asp Asn Trp Arg Ser Glu Leu Tyr Lys Tyr Lys Val
        435                 440                 445

Ile Glu Leu Lys Pro Leu Gly Ile Ala Pro Thr Gly Ala Lys Glu Arg
    450                 455                 460

Val Val Glu Arg Glu Glu Arg Ala Val Gly Ile Gly Ala Val Phe Leu
465                 470                 475                 480

Gly Phe Leu Gly Ala Ala Gly Ser Thr Met Gly Ala Ala Ser Leu Thr
                485                 490                 495

Leu Thr Val Gln Ala Arg Gln Leu Leu Ser Ser Ile Val Gln Gln Gln
            500                 505                 510

Ser Asn Leu Leu Arg Ala Ile Glu Ala Gln Gln His Met Leu Gln Leu
        515                 520                 525
```

```
Thr Val Trp Gly Ile Lys Gln Leu Gln Thr Arg Val Leu Ala Ile Glu
            530                 535                 540

Arg Tyr Leu Lys Asp Gln Gln Leu Leu Gly Ile Trp Gly Cys Ser Gly
545                 550                 555                 560

Lys Leu Ile Cys Thr Thr Asn Val Pro Trp Asn Ser Ser Trp Ser Asn
                565                 570                 575

Lys Ser Gln Thr Asp Ile Trp Asn Asn Met Thr Trp Met Glu Trp Asp
                580                 585                 590

Arg Glu Ile Ser Asn Tyr Thr Asp Thr Ile Tyr Arg Leu Leu Glu Asp
            595                 600                 605

Ser Gln Thr Gln Gln Glu Lys Asn Glu Lys Asp Leu Leu Ala Leu Asp
610                 615                 620

Ser Trp Lys Asn Leu Trp Ser Trp Phe Asp Ile Ser Asn Trp Leu Trp
625                 630                 635                 640

Tyr Ile Lys Ser Arg Ile Glu Gly Arg Gly Ser Gly Gly Tyr Ile Pro
                645                 650                 655

Glu Ala Pro Arg Asp Gly Gln Ala Tyr Val Arg Lys Asp Gly Glu Trp
                660                 665                 670

Val Leu Leu Ser Thr Phe Leu
            675

<210> SEQ ID NO 7
<211> LENGTH: 695
<212> TYPE: PRT
<213> ORGANISM: Artificial Sequence
<220> FEATURE:
<223> OTHER INFORMATION: Mosaic gp140

<400> SEQUENCE: 7

Ala Gly Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
                20                  25                  30

Thr Glu Val His Asn Val Trp Ala Thr His Ala Cys Val Pro Thr Asp
            35                  40                  45

Pro Asn Pro Gln Glu Val Val Leu Glu Asn Val Thr Glu Asn Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Asn Cys Thr Asp Asp Val Arg Asn Val Thr Asn Asn Ala
                100                 105                 110

Thr Asn Thr Asn Ser Ser Trp Gly Glu Pro Met Glu Lys Gly Glu Ile
            115                 120                 125

Lys Asn Cys Ser Phe Asn Ile Thr Thr Ser Ile Arg Asn Lys Val Gln
130                 135                 140

Lys Gln Tyr Ala Leu Phe Tyr Lys Leu Asp Val Val Pro Ile Asp Asn
145                 150                 155                 160

Asp Ser Asn Asn Thr Asn Tyr Arg Leu Ile Ser Cys Asn Thr Ser Val
                165                 170                 175

Ile Thr Gln Ala Cys Pro Lys Val Ser Phe Glu Pro Ile Pro Ile His
            180                 185                 190

Tyr Cys Ala Pro Ala Gly Phe Ala Ile Leu Lys Cys Asn Asp Lys Lys
        195                 200                 205
```

-continued

```
Phe Asn Gly Thr Gly Pro Cys Thr Asn Val Ser Thr Val Gln Cys Thr
210                 215                 220

His Gly Ile Arg Pro Val Val Ser Thr Gln Leu Leu Asn Gly Ser
225                 230                 235                 240

Leu Ala Glu Glu Val Val Ile Arg Ser Glu Asn Phe Thr Asn Asn
                245                 250                 255

Ala Lys Thr Ile Met Val Gln Leu Asn Val Ser Val Glu Ile Asn Cys
            260                 265                 270

Thr Arg Pro Asn Asn Asn Thr Arg Lys Ser Ile His Ile Gly Pro Gly
                275                 280                 285

Arg Ala Phe Tyr Thr Ala Gly Asp Ile Ile Gly Asp Ile Arg Gln Ala
290                 295                 300

His Cys Asn Ile Ser Arg Ala Asn Trp Asn Asn Thr Leu Arg Gln Ile
305                 310                 315                 320

Val Glu Lys Leu Gly Lys Gln Phe Gly Asn Asn Lys Thr Ile Val Phe
                325                 330                 335

Asn His Ser Ser Gly Gly Asp Pro Glu Ile Val Met His Ser Phe Asn
            340                 345                 350

Cys Gly Gly Glu Phe Phe Tyr Cys Asn Ser Thr Lys Leu Phe Asn Ser
        355                 360                 365

Thr Trp Thr Trp Asn Asn Ser Thr Trp Asn Asn Thr Lys Arg Ser Asn
    370                 375                 380

Asp Thr Glu Glu His Ile Thr Leu Pro Cys Arg Ile Lys Gln Ile Ile
385                 390                 395                 400

Asn Met Trp Gln Glu Val Gly Lys Ala Met Tyr Ala Pro Pro Ile Arg
                405                 410                 415

Gly Gln Ile Arg Cys Ser Ser Asn Ile Thr Gly Leu Leu Leu Thr Arg
            420                 425                 430

Asp Gly Gly Asn Asp Thr Ser Gly Thr Glu Ile Phe Arg Pro Gly Gly
        435                 440                 445

Gly Asp Met Arg Asp Asn Trp Arg Ser Glu Leu Tyr Lys Tyr Lys Val
    450                 455                 460

Val Lys Ile Glu Pro Leu Gly Val Ala Pro Thr Lys Ala Lys Glu Arg
465                 470                 475                 480

Val Val Gln Arg Glu Glu Arg Ala Val Gly Ile Gly Ala Val Phe Leu
                485                 490                 495

Gly Phe Leu Gly Ala Ala Gly Ser Thr Met Gly Ala Ala Ser Met Thr
            500                 505                 510

Leu Thr Val Gln Ala Arg Leu Leu Leu Ser Gly Ile Val Gln Gln Gln
        515                 520                 525

Asn Asn Leu Leu Arg Ala Ile Glu Ala Gln Gln His Leu Leu Gln Leu
    530                 535                 540

Thr Val Trp Gly Ile Lys Gln Leu Gln Ala Arg Val Leu Ala Val Glu
545                 550                 555                 560

Arg Tyr Leu Lys Asp Gln Gln Leu Leu Gly Ile Trp Gly Cys Ser Gly
                565                 570                 575

Lys Leu Ile Cys Thr Thr Thr Val Pro Trp Asn Ala Ser Trp Ser Asn
            580                 585                 590

Lys Ser Leu Asp Lys Ile Trp Asn Asn Met Thr Trp Met Glu Trp Glu
        595                 600                 605

Arg Glu Ile Asn Asn Tyr Thr Ser Leu Ile Tyr Thr Leu Ile Glu Glu
    610                 615                 620
```

Ser Gln Asn Gln Gln Glu Lys Asn Glu Gln Glu Leu Leu Glu Leu Asp
625                 630                 635                 640

Lys Trp Ala Ser Leu Trp Asn Trp Phe Asp Ile Ser Asn Trp Leu Trp
            645                 650                 655

Tyr Ile Lys Ser Arg Ile Glu Gly Arg Gly Ser Gly Gly Tyr Ile Pro
        660                 665                 670

Glu Ala Pro Arg Asp Gly Gln Ala Tyr Val Arg Lys Asp Gly Glu Trp
    675                 680                 685

Val Leu Leu Ser Thr Phe Leu
690                 695

<210> SEQ ID NO 8
<211> LENGTH: 2055
<212> TYPE: DNA
<213> ORGANISM: Artificial Sequence
<220> FEATURE:
<223> OTHER INFORMATION: Mos1Env (nucleic acid)

<400> SEQUENCE: 8

```
atgcgggtga ccggcatccg gaagaactac cagcacctgt ggcggtgggg caccatgctg      60
ctgggcatcc tgatgatttg ctctgccgcc ggaaagctgt gggtgaccgt gtactacggc     120
gtgcccgtgt ggaaagaggc caccaccacc ctgttctgcg ccagcgacgc caaggcctac     180
gacaccgagg tgcacaacgt gtgggccacc acgcctgcg tgcccaccga ccccaacccc     240
caggaagtgg tcctggaaaa cgtgaccgag aacttcaaca tgtggaagaa caacatggtg     300
gagcagatgc acgaggacat catcagcctg tgggaccaga gcctgaagcc ctgcgtgaag     360
ctgacccccc tgtgcgtgac cctgaactgc accgacgacg tgcggaacgt gaccaacaac     420
gccaccaaca ccaacagcag ctggggcgag cctatggaaa agggcgagat caagaactgc     480
agcttcaaca tcaccaccctc catccggaac aaggtgcaga agcagtacgc cctgttctac     540
aagctggacg tggtgcccat cgacaacgac agcaacaaca ccaactaccg gctgatcagc     600
tgcaacacca gcgtgatcac ccaggcctgc cccaaggtgt ccttcgagcc catccccatc     660
cactactgcg cccctgccgg cttcgccatc ctgaagtgca acgacaagaa gttcaacggc     720
accggcccct gcaccaacgt gagcaccgtg cagtgcaccc acggcatccg gcccgtggtg     780
tccacccagc tgctgctgaa cggcagcctg gccgaggaag aggtggtgat cagaagcgag     840
aatttcacca acaatgccaa gaccatcatg gtgcagctga acgtgagcgt ggagatcaac     900
tgcacccggc caacaacaa cacccggaag agcatccaca tcggccctgg cagggccttc     960
tacacagccg gcgacatcat cggcgacatc cggcaggccc actgcaacat cagccgggcc    1020
aactggaaca cacccctgcg gcagatcgtg gagaagctgg gcaagcagtt cggcaacaac    1080
aagaccatcg tgttcaacca gcagcggc ggagaccccg agatcgtgat gcacagcttc    1140
aactgtggcg gcgagttctt ctactgcaac agcaccaagc tgttcaacag cacctggacc    1200
tggaacaact ccacctggaa taacaccaag cggagcaacg acaccgaaga gcacatcacc    1260
ctgccctgcc ggatcaagca gattatcaat atgtggcagg aggtcggcaa ggccatgtac    1320
gcccctccca tccggggcca gatccggtgc agcagcaaca tcaccggcct gctgctgacc    1380
cgggacggcg gcaacgatac cagcggcacc gagatcttcc ggcctggcgg cggagatatg    1440
cgggacaact ggcggagcga gctgtacaag tacaaggtgg tgaagatcga gcccctgggc    1500
gtggctccca ccaaggccaa gcggcgggtg gtgcagagcg agaagagcgc cgtgggcatc    1560
ggcgccgtgt ttctgggctt cctgggagcc gccggaagca ccatgggagc cgccagcatg    1620
```

```
accctgaccg tgcaggcccg gctgctgctg tccggcatcg tgcagcagca gaacaacctg   1680
ctccgggcca tcgaggccca gcagcacctg ctgcagctga ccgtgtgggg catcaagcag   1740
ctgcaggcca gggtgctggc cgtggagaga tacctgaagg atcagcagct cctggggatc   1800
tggggctgca cggcaagct gatctgcacc accaccgtgc cctggaacgc cagctggtcc   1860
aacaagagcc tggacaagat ctggaacaat atgacctgga tggaatggga gcgcgagatc   1920
aacaattaca ccagcctgat ctacaccctg atcgaggaaa gccagaacca gcaggaaaag   1980
aacgagcagg aactgctgga actggacaag tgggccagcc tgtggaactg gttcgacatc   2040
agcaactggc tgtgg                                                    2055
```

<210> SEQ ID NO 9
<211> LENGTH: 2052
<212> TYPE: DNA
<213> ORGANISM: Artificial Sequence
<220> FEATURE:
<223> OTHER INFORMATION: Mos2Env (nucleic acid)

<400> SEQUENCE: 9

```
atgagagtgc ggggcatcca gcggaactgg ccccagtggt ggatctgggg catcctgggc     60
ttttggatga tcatcatctg ccgggtgatg ggcaacctgt gggtgaccgt gtactacggc    120
gtgcccgtgt ggaaagaggc caagaccacc ctgttctgcg ccagcgacgc caaggcctac    180
gagaaagagg tgcacaacgt gtgggccacc cacgcctgcg tgcccaccga ccccaacccc    240
caggaaatgg tcctggaaaa cgtgaccgag aacttcaaca tgtggaagaa cgacatggtg    300
gaccagatgc acgaggacat catccggctg tgggaccaga gcctgaagcc ctgcgtgaag    360 ctgaccccc tgtgcgtgac cctggaatgc cggaacgtga aaacgtgag cagcaacggc    420 acctacaaca tcatccacaa cgagacctac aaagagatga gaactgcag cttcaacgcc    480 accaccgtgg tggaggaccg gaagcagaag gtgcacgccc tgttctaccg gctggacatc    540
gtgcccctgg acgagaacaa cagcagcgag aagtccagcg agaacagctc cgagtactac    600
cggctgatca actgcaacac cagcgccatc acccaggcct gccccaaggt gtccttcgac    660
cccatcccca tccactactg cgcccctgcc ggctacgcca tcctgaagtg caacaacaag    720
accttcaacg gcaccggccc ctgcaacaac gtgagcaccg tgcagtgcac ccacggcatc    780
aagcccgtgg tgtccaccca gctgctgctg aacggcagcc tggccgagga agagatcatc    840
atccggtccg agaacctgac caacaacgcc aagaccatca tcgtgcacct gaatgagacc    900
gtgaacatca cctgcacccg gcccaacaac aacacccgga gagcatccg gatcggccct    960 ggccagacct tttacgccac cggcgacatc atcggcgaca tccggcaggc ccactgcaac   1020
ctgagccggg acgctggaa caagaccctg caggcgtga agaagaagct ggccgagcac   1080
ttccccaata gaccatcaa cttcaccagc agcagcggcg gagacctgga aatcaccacc   1140
cacagcttca actgcagggg cgagttcttc tactgcaata cctccggcct gttcaatggc   1200
acctacatgc ccaacggcac caacagcaac agcagcagca acatcacccct gccctgccgg   1260 atcaagcaga tcatcaatat gtggcaggag gtcggcaggg ccatgtacgc ccctcccatc   1320
gccggcaata tcacctgccg gtccaacatc accggcctgc tgctgaccag ggacggcggc   1380
agcaacaacg gcgtgcctaa cgacaccgag accttccggc ctggcggcgg agatatgcgg   1440
aacaactggc ggagcgagct gtacaagtac aaggtggtgg aggtgaagcc cctgggcgtg   1500
gctcctaccg aggccaagcg gcgggtggtg gagagcgaga gagcgccgt gggcatcggc   1560
```

```
gccgtgtttc tgggcattct gggagccgcc ggaagcacca tgggagccgc cagcatcacc    1620
ctgaccgtgc aggcccggca gctgctgtcc ggcatcgtgc agcagcagag caacctgctg    1680
agagccatcg aggcccagca gcacatgctg cagctgaccg tgtggggcat caagcagctg    1740
cagacccggg tgctggccat cgagagatac ctgcaggatc agcagctcct gggcctgtgg    1800
ggctgcagcg gcaagctgat ctgcaccacc gccgtgccct ggaacaccag ctggtccaac    1860
aagagccaga ccgacatctg gacaacatg acctggatgc agtgggacaa agagatcggc     1920
aactacaccg gcgagatcta caggctgctg aagagagcc agaaccagca ggaaaagaac     1980
gagaaggacc tgctggcccct ggacagctgg aagaacctgt ggaactggtt cgacatcacc   2040
aactggctgt gg                                                        2052
```

<210> SEQ ID NO 10
<211> LENGTH: 2133
<212> TYPE: DNA
<213> ORGANISM: Artificial Sequence
<220> FEATURE:
<223> OTHER INFORMATION: Mos2SEnv (nucleic acid)

<400> SEQUENCE: 10

```
atgagagtgc ggggcatgct gagaaactgg cagcagtggt ggatctggtc cagcctgggc      60
ttctggatgc tgatgatcta cagcgtgatg ggcaacctgt gggtcaccgt gtactacggc     120
gtgcccgtgt ggaaggacgc caagaccacc ctgttttgcg cctccgatgc aaggcctac     180 gagaaagagg tgcacaacgt ctgggccacc cacgcctgtg tgcccaccga ccccaatccc    240
caggaaatcg tcctgggcaa cgtgaccgag aacttcaaca tgtggaagaa cgacatggtc    300
gatcagatgc acgaggacat catctcccctg tgggacgcct ccctggaacc ctgcgtgaag    360
ctgacccctc tgtgcgtgac cctgaactgc cggaacgtgc caacgtgtc cagcaacggc    420 acctacaaca tcatccacaa cgagacatac aaagagatga agaactgcag cttcaacgct    480
accaccgtgg tcgaggaccg gaagcagaag gtgcacgccc tgttctaccg gctggacatc    540
gtgcccctgg acgagaacaa cagcagcgag aagtcctccg agaacagctc cgagtactac    600
agactgatca actgcaacac cagcgccatc acccaggcct gccccaaggt gtccttcgac    660
cctatcccca tccactactg cgcccctgcc ggctacgcca tcctgaagtg caacaacaag    720
accttcaatg gcaccggccc ctgcaacaat gtgtccaccg tgcagtgcac ccacggcatc    780
aagcccgtgg tgtctaccca gctgctgctg aacggcagcc tggccgagga agagatcatt    840
atcagaagcg agaacctgac caacaacgcc aaaaccatca tcgtccacct gaacgaaacc    900
gtgaacatca cctgtacccg gcctaacaac aacacccgga agtccatccg gatcggccct    960
ggccagacct tttacgccac cggcgatatt atcggcgaca tccggcaggc ccactgcaat    1020
ctgagccggg acggctggaa caagacactg caggggcgtca gaagaagct ggccgaacac    1080 ttccctaaca agactatcaa gttcgcccct cactctggcg cgacctgga atcaccacc     1140 cacaccttca actgtcgggg cgagttcttc tactgcaata cctccaacct gttcaacgag    1200
agcaacatcg agcggaacga cagcatcatc acactgcctt gccggatcaa gcagattatc    1260
aatatgtggc aggaagtggg cagagccatc tacgcccctc caatcgccgg caacatcaca    1320
tgccggtcca atatcaccgg cctgctgctc accagagatg cgggctccaa caatggcgtg    1380
ccaaacgaca ccgagacatt cagacccggg ggaggcgaca tgcggaacaa ttggcggagc    1440
gagctgtaca gtacaaggt ggtggaagtg aagcccctgg gcgtggcccc taccgaggcc    1500
aagagaagag tggtcgaacg cgagaagcgg gccgtgggaa tcggagccgt gtttctggga    1560
```

```
atcctgggag ccgctggctc taccatgggc gctgcctcta tcaccctgac agtgcaggcc    1620
agacagctgc tcagcggcat cgtgcagcag cagagcaacc tgctgagagc cattgaggcc    1680
cagcagcaca tgctgcagct gaccgtgtgg ggcattaagc agctccagac acgggtgctg    1740
gccatcgaga gatacctgca ggatcagcag ctcctgggcc tgtggggctg tagcggcaag    1800
ctgatctgta ccaccgccgt gccctggaat acctcttgga gcaacaagag ccagaccgac    1860
atctgggaca catgacctg gatgcagtgg gacaaagaaa tcggcaacta taccggcgag    1920
atctatagac tgctggaaga gtcccagaac cagcaggaaa agaacgagaa ggacctgctg    1980
gccctggatt cttggaacaa tctgtggaac tggttcagca tctccaagtg gctgtggtac    2040
atcaagatct tcatcatgat cgtgggcggc ctgatcggcc tgcggatcat ctttgccgtg    2100
ctgagcatcg tgaaccgcgt gcggcagggc tac                                 2133

<210> SEQ ID NO 11
<211> LENGTH: 4050
<212> TYPE: DNA
<213> ORGANISM: Artificial Sequence
<220> FEATURE:
<223> OTHER INFORMATION: SEQ ID NO: 11

<400> SEQUENCE: 11
atgggagcca gagccagcgt gctgtccgga ggggagctgg accgctggga gaagatcagg      60
ctgaggcctg agggaagaa gaagtacagg ctgaagcaca tcgtgtgggc cagcagagag     120
ctggaacggt ttgccgtgaa ccctggcctg ctggaaacca gcgagggctg taggcagatt     180
ctgggacagc tgcagcccag cctgcagaca ggcagcgagg aactgcggag cctgtacaac     240
accgtggcca ccctgtactg cgtgcaccag cggatcgaga tcaaggacac caaagaagcc     300
ctggaaaaga tcgaggaaga gcagaacaag agcaagaaga agcccagca ggctgccgct     360 gacacaggca acagcagcca ggtgtcccag aactaccca tcgtgcagaa catccaggga     420
cagatggtgc accaggccat cagccctcgg accctgaacg cctgggtgaa ggtggtggag     480
gaaaaggcct tcagccctga ggtgatcccc atgttctctg ccctgagcga gggagccaca     540
ccccaggacc tgaacaccat gctgaacacc gtggagggc accaggctgc catgcagatg     600
ctgaaagaga caatcaacga ggaagctgcc gagtgggaca gggtccaccc agtgcacgct     660
ggacctatcg ctcctggcca gatgagagag cccagaggca gcgatattgc tggcaccacc     720
tccacactgc aggaacagat cggctggatg accaacaacc ctccatccc tgtgggagag     780 atctacaagc ggtggatcat tctgggactg aacaagatcg tgcggatgta cagccctgtg     840
agcatcctgg acatcaggca gggacccaaa gagcccttca gggactacgt ggaccggttc     900
tacaagaccc tgagagccga gcaggccagc caggacgtga gaactggat gaccgagaca     960 ctgctggtgc agaacgccaa ccctgactgc aagaccatcc tgaaagccct gggacctgct    1020
gccaccctgg aagagatgat gacagcctgc cagggagtgg gaggacctgg ccacaaggcc    1080
agggtgctgg ccgaggccat gagccaggtg accaactctg ccaccatcat gatgcagaga    1140
ggcaacttcc ggaaccagag aaagaccgtg aagtgcttca actgtggcaa agagggacac    1200
attgccaaga actgcagggc tcccaggaag aaaggctgct ggaagtgcgg aaaagaaggc    1260
caccagatga aggactgcac cgagaggcag gccaacttcc tgggcaagat ctggcctagc    1320
aacaagggca ggcctggcaa cttcctgcag aacagaccg agcccaccgc tcctcccgag    1380
gaaagcttcc ggtttggcga ggaaaccacc ccccctagcc agaagcagga acccatcgac    1440
```

```
aaagagatgt accctctggc cagcctgaag agcctgttcg gcaacgaccc cagcagccag      1500
atggctccca tcagcccaat cgagacagtg cctgtgaagc tgaagcctgg catggacgga      1560
cccagggtga agcagtggcc tctgaccgag gaaaagatca agccctgac agccatctgc       1620 gaggaaatgg aaaagagggg caagatcacc aagatcggac ccgagaaccc ctacaacacc      1680
cctgtgttcg ccatcaagaa gaaagacagc accaagtgga ggaaactggt ggacttcaga      1740
gagctgaaca gcggaccca ggacttctgg gaggtgcagc tgggcatccc tcaccctgct       1800
ggcctgaaga aaagaaaag cgtgaccgtg ctggctgtgg gagatgccta cttcagcgtg       1860
cctctggacg agggcttccg gaagtacaca gccttcacca tccccagcac caacaacgag      1920
acacctggca tcagatacca gtacaacgtg ctgcctcagg gctggaaagg cagccctgcc      1980
atcttccagt gcagcatgac cagaatcctg gaacccttca gagccaagaa ccctgagatc      2040
gtgatctacc agtatatggc tgccctctac gtgggcagcg acctggaaat cggacagcac      2100
agagccaaaa tcgaagaact ccgcgagcac ctgctgaagt ggggattcac caccccctgac    2160 aagaagcacc agaaagagcc tccccttcctg tggatgggct acgagctgca ccctgacaag    2220
tggaccgtgc agcccatcca gctgccagag aaggactcct ggaccgtgaa cgacatccag     2280
aaactggtcg gcaagctgaa ctgggccagc cagatctacc ctggcatcaa agtcagacag     2340
ctgtgtaagc tgctgagggg agccaaagca ctgaccgaca tcgtgcctct gacagaagaa     2400
gccgagctgg aactggccga gaacagagag atcctgaaag aacccgtgca cggagtgtac     2460
tacgacccct ccaaggacct gattgccgag atccagaaac agggacacga ccagtggacc     2520
taccagatct atcaggaacc tttcaagaac ctgaaaacag gcaagtacgc caagatgcgg     2580
acagcccaca ccaacgacgt gaagcagctg accgaagccg tgcagaaaat cgccatggaa     2640
agcatcgtga tctggggaaa gacacccaag ttcaggctgc ccatccagaa agagacatgg     2700
gaaacctggt ggaccgacta ctggcaggcc acctggattc ccgagtggga gttcgtgaac     2760
accccacccc tggtgaagct gtggtatcag ctggaaaagg accctatcgc tggcgtggag     2820
acattctacg tggctggagc tgccaacaga gagacaaagc tgggcaaggc tggctacgtg     2880
accgacagag gcagacagaa aatcgtgagc ctgaccgaaa ccaccaacca gaaaacagcc     2940
ctgcaggcca tctatctggc actgcaggac agcggaagcg aggtgaacat cgtgacagcc     3000
agccagtatg ccctgggcat catccaggcc cagcctgaca gagcgagag cgagctggtg      3060 aaccagatca tcgagcagct gatcaagaaa gaacgggtgt acctgagctg ggtgccagcc     3120
cacaagggca tcgagggaa cgagcaggtg acaagctgg tgtccagcgg aatccggaag       3180
gtgctgttcc tggacggcat cgataaagcc caggaagagc acgagaagta ccacagcaat     3240
tggagagcca tggccagcga cttcaacctg cctcccgtgg tggccaaaga aatcgtggcc     3300
agctgcgacc agtgccagct gaaaggcgag gccatgcacg gacaggtgga ctgctcccct    3360
ggcatctggc agctggcatg cacccaccctg gaaggcaaga tcattctggt ggccgtgcac    3420
gtggccagcg gatacatcga gccgaagtg atccctgccg acagggca ggaaacagcc        3480 tacttcatcc tgaagctggc tggcagatgg cctgtgaagg tgatccacac agccaacggc     3540
agcaacttca cctctgctgc cgtgaaggct gcctgttggt gggctggcat tcagcaggaa     3600
tttggcatcc cctacaatcc ccagtctcag ggagtggtgg ccagcatgaa caaagagctg     3660
aagaagatca tcggacaggt cagggatcag gccgagcacc tgaaaactgc cgtccagatg     3720
gccgtgttca tccacaactt caagcggaag ggagggatcg agggtactc tgctggcgag     3780 cggatcatcg acatcattgc caccgatatc cagaccaaag agctgcagaa acagatcatc     3840
```

<210> SEQ ID NO 12
<211> LENGTH: 4023
<212> TYPE: DNA
<213> ORGANISM: Artificial Sequence
<220> FEATURE:
<223> OTHER INFORMATION: Mos2GagPol (nucleic acid)

<400> SEQUENCE: 12

```
aagatccaga acttcagggt gtactacagg gacagcaggg accccatctg aagggacct     3900 gccaagctgc tgtggaaagg cgaaggagcc gtcgtcatcc aggacaacag cgacatcaag   3960
gtggtgccca cacggaaggt gaaaatcatc aaggactacg gcaaacagat ggctggagcc   4020
gactgtgtcg ctggcaggca ggacgaggac                                    4050
```

```
atgggagcca gagccagcat cctgcgagga gggaagctgg acaagtggga gaagatcagg    60
ctgaggcctg gagggaagaa acactacatg ctgaagcacc tggtctgggc cagcagagag   120
ctggaacggt ttgccctcaa tcctggcctg ctggaaacca gcgagggctg caagcagatc   180
atcaagcagc tgcagcctgc cctgcagaca ggcaccgagg aactgcggag cctgttcaac   240
accgtggcca ccctgtactg cgtgcatgcc gagatcgaag tgagggacac caagaagcc    300 ctggacaaga tcgaggaaga gcagaacaag agccagcaga aaccccagca ggccaaagaa   360
gccgacggca aggtctccca gaactacccc atcgtgcaga acctgcaggg acagatggtg   420
caccagccca tcagccctcg acactgaat gcctgggtga aggtgatcga ggaaaaggcc   480
ttcagccctg aggtgatccc catgttcaca gccctgagcg agggagccac accccaggac   540
ctgaacacca tgctgaacac cgtgggaggg caccaggctg ccatgcagat gctgaaggac   600
accatcaacg aggaagctgc cgagtgggac aggctgcacc ctgtgcacgc tggacctgtg   660
gctcctggcc agatgagaga gcccagaggc agcgatattg ctggcaccac ctccaatctg   720
caggaacaga tcgcctggat gaccagcaac cctcccatcc ctgtgggaga catctacaag   780
cggtggatca tcctgggact gaacaagatc gtgcggatgt acagccctac ctccatcctg   840
gacatcaagc agggacccaa agagcctttc aggactacg tggaccggtt cttcaagacc   900
ctgagagccg agcaggccac ccaggacgtg aagaactgga tgaccgacac cctgctggtg   960
cagaacgcca ccctgactg caagaccatc ctgagagccc tgggacctgg agccaccctg  1020
gaagagatga tgacagcctg ccaggagtgg gaggaccct ctcacaaggc tagggtgctg  1080
gccgaggcca tgagccagac caacagcacc atcctgatgc agcggagcaa cttcaagggc  1140
agcaagcgga tcgtgaagtg cttcaactgt ggcaaagagg acacattgc cagaaactgt  1200 agggcaccca ggaagaaagg ctgctggaag tgcggaaaag aaggccacca gatgaaggac  1260
tgcaccgaga gcaggccaa cttcctgggc aagatctggc ctagccacaa gggcagacct  1320
ggcaacttcc tgcagagcag acccgagccc accgctcctc agccgagag cttccggttc  1380 gaggaaacca cccctgctcc caagcaggaa cctaaggaca gagagcctct gaccagcctg  1440
agaagcctgt tcggcagcga ccctctgagc cagatggctc ccatctcccc tatcgagaca  1500
gtgcctgtga agctgaagcc tggcatggac ggacccaagg tgaaacagtg cctctgacc  1560 gaggaaaaga tcaaagccct ggtggagatc tgtaccgaga tggaaaaaga gggcaagatc  1620
agcaagatcg accccgagaa cccctacaac accccctatct tcgccatcaa gaagaaagac  1680
agcaccaagt ggaggaaact ggtggacttc agagagctga acaagcggac ccaggacttc  1740
tgggaggtgc agctgggcat ccctcaccct gctggcctga gaaaaagaa aagcgtgacc  1800
```

```
gtgctggccg tgggagatgc ctacttcagc gtgcctctgg acgaggactt cagaaagtac    1860
acagccttca ccatcccag catcaacaac gagacacctg gcatcagata ccagtacaac    1920
gtgctgcctc agggatggaa gggctctcct gcaatcttcc agagcagcat gaccaagatc   1980
ctggaaccct tccggaagca gaaccctgac atcgtgatct accagtacat ggcagccctg   2040
tacgtcggca gcgacctgga aatcggacag caccggacca agatcgaaga actcaggcag   2100
cacctgctgc ggtggggatt caccacccct gacaagaagc accagaaaga gcctcccttc   2160
ctgtggatgg gctacgagct gcacccagac aagtggaccg tgcagcccat cgtgctgcct   2220
gagaaggact cctggaccgt gaacgacatc cagaaactgg tcggcaagct gaactgggcc   2280
agccagatct acgctggcat caaagtgaag cagctgtgta gctcctgag aggcaccaaa    2340
gccctgaccg aggtggtgcc actgacagag gaagccgagc tggaactggc cgagaacaga   2400
gagatcctga agaacccgt gcacggagtg tactacgacc ccagcaagga cctgattgcc    2460
gagatccaga agcagggaca gggacagtgg acctaccaga tctaccagga acccttcaag   2520
aacctgaaaa caggcaagta cgccaggatg aggggagccc acaccaacga cgtcaaacag   2580
ctgaccgaag ccgtgcagaa gatcgccacc gagagcatcg tgatttgggg aaagacccc    2640
aagttcaagc tgcccatcca gaaagagaca tgggaggcct ggtggaccga gtactggcag   2700
gccacctgga ttcccgagtg ggagttcgtg aacacccac ccctggtgaa gctgtggtat    2760
cagctggaaa agaacccat cgtgggagcc gagacattct acgtggctgg agctgccaac   2820
agagagacaa agctgggcaa ggctggctac gtgaccgaca gaggcaggca gaaagtggtg   2880
tccctgaccg ataccaccaa ccagaaaaca gccctgcagg ccatccacct ggctctgcag   2940
gactctggcc tggaagtgaa catcgtgaca gccagccagt atgccctggg catcattcag   3000
gcacagcctg acaagagcga gagcgagctg gtgtctcaga tcattgagca gctgatcaag   3060
aaagaaaagg tgtacctggc ctgggtgcca gcccacaagg ggatcggagg gaacgagcag   3120
gtggacaagc tggtgtccag gggcatccgg aaggtgctgt ttctggacgg catcgacaaa   3180
gcccaggaag agcacgagaa gtaccacagc aattggagag ccatggccag cgagttcaac   3240
ctgcctccca tcgtggccaa agaaatcgtg gcctcttgcg acaagtgcca gctgaaaggc   3300
gaggccattc acggacaggt ggactgcagc ccaggcatct ggcagctggc ctgcacccac   3360
ctggaaggca aggtgatcct ggtggccgtg cacgtggcct ctggatacat cgaagccgaa   3420
gtgatccctg ccgagacagg ccaggaaaca gcctacttcc tgctgaagct ggctggcagg   3480
tggcctgtga aaaccatcca cacagccaac ggcagcaact tcacctctgc caccgtgaag   3540
gctgcctgtt ggtgggctgg cattaagcag gaatttggca tccctacaa ccctcagtct   3600
cagggagtgg tggcctccat caacaaagag ctgaagaaga tcatcggaca ggtcagggat   3660
caggccgagc atctgaaaac agccgtccag atggccgtgt tcatccacaa cttcaagcgg   3720
aagggaggga tcgagagta ctctgctggc gagaggatcg tggacattat cgccagcgat   3780
atccagacca agaactgca gaagcagatc acaaagatcc agaacttcag ggtgtactac   3840
agggacagcg agatcccct gtggaaggga cctgccaagc tgctgtggaa aggcgaagga   3900
gccgtcgtca tccaggacaa cagcgacatc aaggtggtgc ccagacggaa ggccaagatc   3960
atcagagact acggcaaaca gatggctggc gacgactgcg tcgcctctag gcaggacgag   4020
gac                                                                 4023
```